(12) United States Patent
Park et al.

(10) Patent No.: US 9,943,525 B2
(45) Date of Patent: Apr. 17, 2018

(54) COMPOSITION FOR REDUCING CELL SENESCENCE COMPRISING RHO-KINASE INHIBITOR AND USE THEREOF

(71) Applicant: Samsung Electronics Co., Ltd., Suwon-si, Gyeonggi-do (KR)

(72) Inventors: Joontae Park, Seoul (KR); Hyuntae Kang, Seoul (KR); Chulwon Jung, Seoul (KR); Kobong Choi, Osan-si (KR); Sangchul Park, Seongnam-si (KR); Hyojei Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 2 days.

(21) Appl. No.: 14/814,312

(22) Filed: Jul. 30, 2015

(65) Prior Publication Data

US 2016/0095864 A1 Apr. 7, 2016

(30) Foreign Application Priority Data

Oct. 6, 2014 (KR) ........................ 10-2014-0134481

(51) Int. Cl.
| | |
|---|---|
| *A61K 31/551* | (2006.01) |
| *A61K 31/4409* | (2006.01) |
| *A61K 8/49* | (2006.01) |
| *A61Q 19/08* | (2006.01) |
| *A61K 31/4155* | (2006.01) |

(52) U.S. Cl.
CPC ............ *A61K 31/551* (2013.01); *A61K 8/494* (2013.01); *A61K 8/4926* (2013.01); *A61K 8/4946* (2013.01); *A61K 31/4155* (2013.01); *A61K 31/4409* (2013.01); *A61Q 19/08* (2013.01)

(58) Field of Classification Search
CPC ... A61Q 19/08; A61K 31/551; A61K 31/4155
See application file for complete search history.

(56) References Cited

U.S. PATENT DOCUMENTS

| | | | |
|---|---|---|---|
| 7,803,559 | B1 | 9/2010 | Diamond et al. |
| 8,354,384 | B2 | 1/2013 | Slack et al. |
| 8,476,259 | B2 | 7/2013 | Fong |
| 8,637,310 | B2 | 1/2014 | McBride et al. |
| 8,673,840 | B2 | 3/2014 | Chudzinski-Tavassi et al. |
| 2004/0028716 | A1 | 2/2004 | Marks et al. |
| 2005/0096253 | A1 | 5/2005 | Monnier et al. |
| 2005/0222130 | A1 | 10/2005 | Fagot et al. |
| 2007/0049588 | A1 | 3/2007 | Smith et al. |
| 2008/0108568 | A1 | 5/2008 | Stephan et al. |
| 2008/0131375 | A1 | 6/2008 | Gordon et al. |
| 2009/0142839 | A1 | 6/2009 | Primiano |
| 2009/0169585 | A1 | 7/2009 | Sardi |
| 2009/0325929 | A1* | 12/2009 | Li ........................ C07D 471/10 514/212.02 |
| 2011/0003891 | A1 | 1/2011 | Durlach |
| 2011/0034554 | A1* | 2/2011 | Washington ......... A61K 31/135 514/546 |
| 2012/0010196 | A1 | 1/2012 | Qin et al. |
| 2013/0005756 | A1 | 1/2013 | Navratil et al. |
| 2013/0309681 | A1 | 11/2013 | Schlegel et al. |
| 2014/0011889 | A1 | 1/2014 | Sardi |

FOREIGN PATENT DOCUMENTS

| | | |
|---|---|---|
| JP | 2005-206485 A | 8/2005 |
| JP | 2006-327942 A | 12/2006 |
| KR | 2011-0049808 A | 5/2011 |
| KR | 2012-0082626 A | 7/2012 |
| WO | WO 2010/065907 A2 | 6/2010 |
| WO | WO 2010/135004 A1 | 11/2010 |
| WO | WO 2011/149012 A1 | 12/2011 |
| WO | WO 2012/024611 A1 | 2/2012 |
| WO | WO2014/093773 * | 6/2014 |
| WO | WO 2014/093773 A1 | 6/2014 |
| WO | WO 2014/160409 A1 | 10/2014 |

OTHER PUBLICATIONS

Fernandes (Rho kinase as a therapeutic target in the treatment of asthma and chronic obstructive pulmonary disease, 2007, Therapeutic Advances in Respiratory Disease, 1(1), pp. 25-33).*
Allaire (Muscle Nerve. Mar. 2002;25(3):383-9, abstract only).*
Iizuka (Evaluation of Y-27632, a Rho-kinase inhibitor, as a bronchodilator in guinea pigs, European Journal of Pharmacology 406 2000. 273-27.*
Gandham et al., Effects of Y27632 on keratinocyte procurement and wound healing, *Clinical and Experimental Dermatology*, 38: 782-786 (2013).
Georgakopoulou et al., Specific Sustaining as a novel biomarker to detect replicative and stress-induced senescence. A method applicable in cryo-preserved and archival tissues, *Aging*, 5(1):37-50 (2013).
Van Den Bogaard et al., Rho Kinase Inhibitor Y-27632 Prolongs the Life Span of Adult Human Keratinocytes, Enhances Skin Equivalent Development, and Facilitates Lentiviral Transduction, Tissue Engineering, 18 (17-18): 1827-1836 (2012).
European Patent Office, Extended European Search Report in Application No. 15184916.3 dated Dec. 2, 2015.
Chapman et al., "The effect of Rho kinase inhibition on long-term keratinocyte proliferation is rapid and conditional", *Stem Cell Research & Therapy*, 5 (60) 1-11 (2014).
Gandham et al., "Effects of Y27632 on keratinocyte procurement and wound healing", *Clin Exp Dermatol*, 38(7), 782-786 (2013).
Watanabe et al., "A ROCK inhibitor permits survival of dissociated human embryonic stem cells", *Nature Biotechnology*, 25(6) 681-686 (2007).
Bowerman et al., Fasudil improves survival and promotes skeletal muscle development in a mouse model of spinal muscular atrophy, *BMC Medicine*, 10 (24): 1-14 (2012).
European Patent Office, Exam Report for Application No. 15184916.3 dated May 15, 2017, 8 pp.
Feng et al., "Discovery of Substituted 4-(Pyrazol-4-yl)-phenylbenzodioxane-2-carboxamides as Potent and Highly Selective Rho Kinase (ROCK-II) Inhibitors", J. Med. Chem., 51:6642-6645 (2008).
European Patent Office, Exam Report for Application No. 15184916.3 dated Jan. 22, 2018, 10 pp.

* cited by examiner

*Primary Examiner* — San Ming R Hui
(74) *Attorney, Agent, or Firm* — Leydig, Voit & Mayer, Ltd.

(57) ABSTRACT

A composition for reducing cell senescence including a Rho-kinase inhibitor and method of treating a cell senescence-related symptom in mammals.

5 Claims, 24 Drawing Sheets

COMPOSITION FOR REDUCING CELL SENESCENCE COMPRISING RHO-KINASE INHIBITOR AND USE THEREOF

RELATED APPLICATION

This application claims the benefit of Korean Patent Application No. 10-2014-0134481, filed on Oct. 6, 2014, in the Korean Intellectual Property Office, the entire disclosure of which is hereby incorporated by reference.

BACKGROUND

1. Field

The present disclosure relates to compositions for reducing cell senescence, methods of reducing cell senescence in mammals, and methods of treating cell senescence-related symptoms in mammals.

2. Description of the Related Art

Senescence may be defined as a permanent halt of cellular division. Replicative senescence or cellular senescence has been observed as an aging model at the cellular level. When cells are continuously cultured, cells divide a number of times, but aged cells can no longer divide. Senescent cells are resistant against programmed cell death, and some senescent cells are maintained in a non-dividing state for several years.

Rho-kinase is a kinase that belongs to the AGC (PKA/PKG/PKC) family of serine-threonine kinases. Rho-associated protein kinases (i.e., ROCKs) including ROCK1 and ROCK2, are found in mammals, zebrafish, *Xenopus*, and the like. Human ROCK1 has a molecular mass of 150 kDa and is a major downstream effector of small GTPase RhoA. Mammal ROCK includes a kinase domain, a coiled-coil region, and a Pleckstrin homology (PH) domain, which reduces the kinase activity of ROCKs by autoinhibitory intramolecular fold if RhoA-GTP is not present.

Because of the role that ROCKs play in cellular processes associated with cellular senescence, there remains a need to develop compositions and methods of reducing cell senescence with Rho-kinase inhibitors.

SUMMARY

Provided is a method of reducing cell senescence in a mammal includes reducing cell senescence by administering an effective amount of a Rho-kinase inhibitor to the mammal.

Provided is a method of treating a cell senescence-related symptom in a mammal, wherein the method includes treating a cell senescence-related symptom by administering an effective amount of a Rho-kinase inhibitor to the mammal.

Provided is a method of treating an intracellular lipofuscin accumulation-related symptom in a mammal, wherein the method includes treating a lipofuscin accumulation-related symptom by administering an effective amount of a Rho-kinase inhibitor to the mammal.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
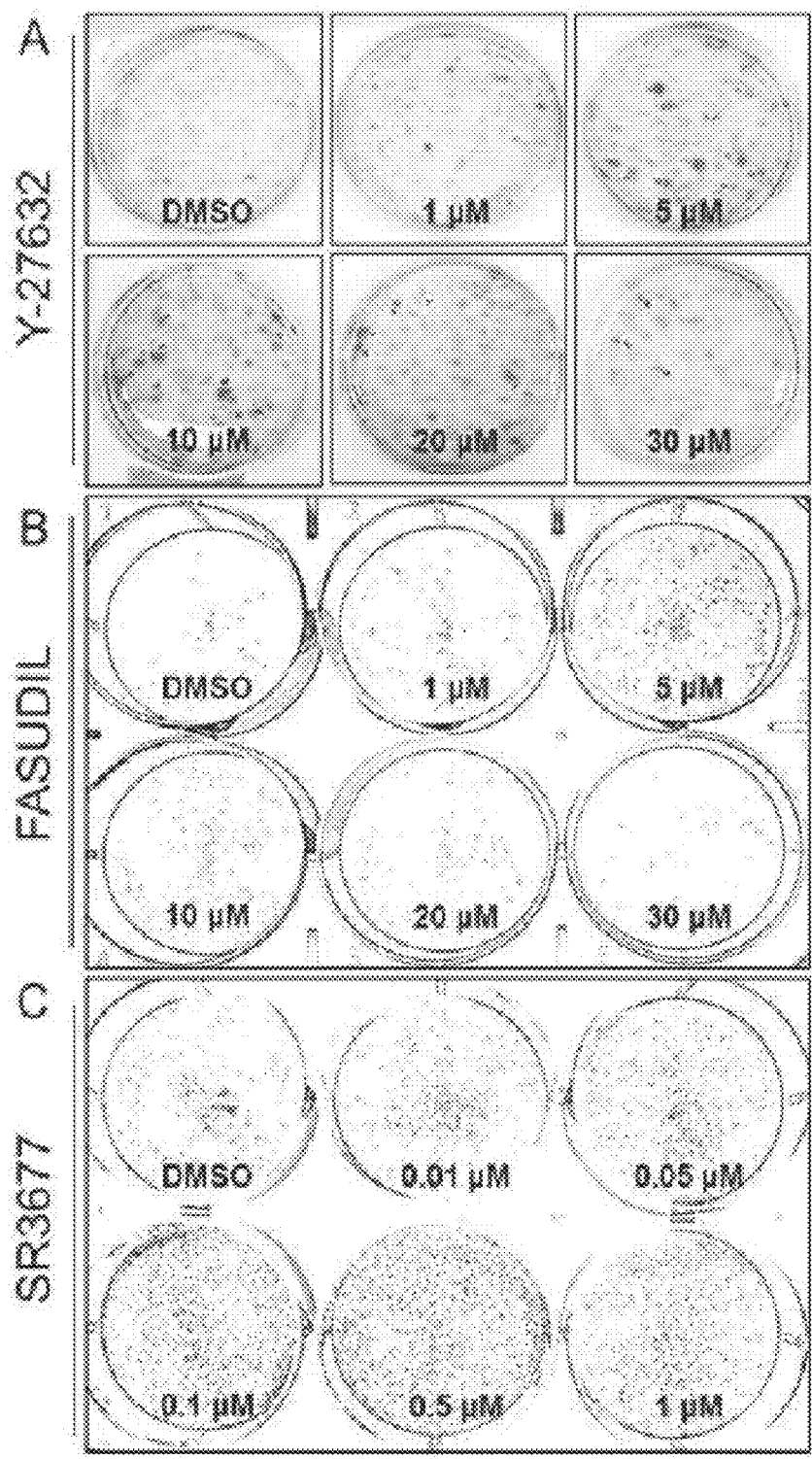
FIG. 1 is an illustration showing cell colony formation of cells exposed to various concentrations of the Rho-kinase inhibitors Y-27632, Fasudil, and SR3677.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list. Additional aspects will be set forth in part in the description which follows and, in part, will be apparent from the description, or may be learned by practice of the presented exemplary embodiments.

Provided is a composition useful for reducing cell senescence wherein the composition includes a Rho-kinase inhibitor as an active ingredient.

Rho-kinase, also known as, "Rho-associated protein kinase (ROCK)", is a kinase belonging to the AGC (PKA/PKG/PKC) family of serine-threonine kinases. ROCKs (e.g., ROCK1 and ROCK2) are found in mammals, zebrafish, *Xenopus*, and the like. Human ROCK1 has a molecular mass of 150 kDa and is a major downstream effector of small GTPase RhoA. Mammal ROCK includes a kinase domain, a coiled-coil region, and a Pleckstrin homology (PH) domain, which reduces the kinase activity of ROCKs by autoinhibitory intramolecular fold if RhoA-GTP is not present.

The Rho-kinase inhibitor may be (1R,4R)-4-((R)-1-aminoethyl)-N-(pyridin-4-yl)cyclohexanecarboxamide (Y-27632), N-[2-[2-(dimethylamino)ethoxy]-4-(1H-pyrazol-4-yl)phenyl]-2,3-dihydro-1,4-benzodioxin-2-carboxamide] (SR3677), 5-(1,4-diazepane-1-sulfonyl)isoquinoline (Fasudil), or any pharmaceutically acceptable salt, stereoisomer, or combination thereof.

Reducing cell senescence includes delaying or preventing senescence of cells, and/or reverting senescent cells to a younger cell state (e.g., a cell state similar to that of a pre-senescent cell). Reducing cell senescence may include enhancing a cell's ability to proliferate, reducing accumulation of lipofuscin, reducing activity of β-galactosidase, reducing the number of mitochondrial reactive oxygen species, increasing mitochondrial membrane potential, and/or reducing duration of G0 and/or G1 phase of the cell cycle. The senescent cells may be myocytes including myoblasts, fibroblasts, cells from a subject suffering Hutchinson-Gilford progeria syndrome, or nerve cells.

The composition may be used to treat cell senescence-related symptoms (i.e., symptoms of cell senescence). Examples of the cell senescence-related symptoms include skin wrinkles, reduced ability to repair wounds, sarcopenia, Hutchinson-Gilford progeria syndrome, or any combination thereof. The cell senescence-related symptoms may be lipofuscin accumulation-related symptoms (i.e., symptoms of lipofuscin accumulation). Examples of the lipofuscin accumulation-related symptoms include neuronal ceroid lipofuscinoses (NCL), age-related macular degeneration, neurofibrillary tangles, Brown atrophy of the heart, Alzheimer's disease, Parkinson's disease, amyotrophic lateral sclerosis (ALS), acromegaly, denervation atrophy, lipid myopathy, and chronic obstructive pulmonary disease (COPD). The cell senescence-related symptoms may also be diseases caused by damaged mitochondria such as an increase in mitochondrial reactive oxygen species, a decrease in mitochondrial membrane potential, or any combination thereof. Also, the cell senescence-related symptoms may be caused by an increased activity of β-galactosidase in cells.

The Rho-kinase inhibitor may be in the form of a pharmaceutically acceptable salt. The pharmaceutically acceptable salt may be an acid addition salt commonly used in the field of pharmaceutical compositions, for example, in the field of cell senescence-related diseases, for example, a salt derived from an inorganic salt such as hydrochloric acid, bromic acid, sulfuric acid, sulfamic acid, phosphoric acid, or nitric acid and a salt derived from an organic salt such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. The salt also includes a salt derived from metal such as lithium, sodium, potassium, magnesium, or calcium. The acid addition salt or metal salt may be manufactured using any known method in the art.

The Rho-kinase inhibitor may be in the form of a solvate. The "solvate" refers to a complex or aggregate formed by one or more solute molecules, i.e., the Rho-kinase inhibitor or a pharmaceutically acceptable salt thereof, and one or more solvent molecules. The solvate may be a complex or aggregate formed by the solute molecules and water, methanol, ethanol, isopropanol, or acetic acid.

The Rho-kinase inhibitor may also be in the form of a stereoisomer. The stereoisomer includes all isomers such as enantiomers and diastereomers. The Rho-kinase inhibitor may be a stereoisomerically pure form or a mixture of at least one stereoisomer, for example, a racemic mixture. A particular stereoisomer may be separated using any method known in the art.

In the composition, the cell may be a cell of a mammal including a human. The mammal may have a cell senescence-related disease.

The composition may further include a pharmaceutically acceptable carrier. In the composition, the "pharmaceutically acceptable carrier" refers to a substance combined with an active ingredient to assist application of the active ingredient, generally, an inert substance. The carrier may include a conventional pharmaceutically acceptable excipient, an additive, or a diluent. For example, the carrier may include at least one selected from the group consisting of a filler, a binder, a disintegrant, a buffer, a preservative, an antioxidant, a lubricant, a flavoring agent, a thickener, a coloring agent, an emulsifier, a suspension, a stabilizer, and an isotonic agent.

The composition may include the Rho-kinase inhibitor or a pharmaceutically acceptable salt or solvate thereof in a therapeutically effective amount. In the composition, the "therapeutically effective amount" refers to an amount sufficient to bring about a desired therapeutic effect in a subject in need of treatment (e.g., an increase in cellular proliferation or a reduction in accumulation of lipofuscin). The term "therapeutically" refers to treating diseases or medical symptoms, such as, cell senescence-related diseases, in subjects, for example, mammals such as humans and includes: (a) prevention of outbreaks of diseases or medical symptoms, i.e., prophylactic treatment of patients; (b) alleviation of diseases or medical symptoms, i.e., removal of or recovery from diseases or medical symptoms in patients; (c) suppression of diseases or medical symptoms, i.e., delaying or stopping the progress of diseases or medical symptoms in a subject; or (d) relief of diseases or medical symptoms in subjects. The "effective amount" may be selected by one of ordinary skill in the art. The "effective amount" may be an amount of about 0.01 mg to about 10,000 mg, about 0.1 mg to about 1,000 mg, about 1 mg to about 100 mg, about 0.01 mg to about 1,000 mg, about 0.01 mg to about 100 mg, about 0.01 mg to about 10 mg, or about 0.01 mg to about 1 mg.

The composition may administered orally or parenterally via intravenous, intraperitoneal, subcutaneous, rectal administration, or local administration. Thus, the composition may be formulated as various formulations such as tablets, capsules, aqueous liquid preparations, or suspensions. In general, an excipient such as lactose and corn starch and a lubricant such as magnesium stearate may be added to tablets for oral administration. In capsules for oral administration, lactose and/or dry corn starch may be used as a diluent. When an aqueous suspension for oral administration is used, an active ingredient may be associated with an emulsifier and/or a suspension. If required, a sweetener and/or flavoring agent may further be added to the formulations. In case of intraneural, intramuscular, intraperitoneal, subcutaneous, and intravenous administration, a sterile solution of the active ingredient is prepared, the pH of the solution is adjusted, and the solution is buffered. In case of intravenous administration, a total concentration of solutes may be adjusted to allow formulations to have isotonicity. The composition may be an aqueous liquid preparation including a pharmaceutically acceptable carrier such as salt water having a pH of 7.4. The solution may be introduced into intramuscular or intraneural blood stream via local bolus injection.

As used herein, the phrases "cell senescence," "senescence of a cell," and "cellular senescence" refer to a cell with a reduced ability to proliferate, an increase in accumulation of lipofuscin, an increase in the activity of β-galactosidase, an increase in mitochondrial reactive oxygen species, a decrease in mitochondrial membrane potentials, and/or an increase in duration of G0 and/or G1 phase of the cells, as compared with a reference cell (e.g., a known non-senescent cell of the same cell type), or a process or condition that causes these characteristics. As used herein, the phrases "young cell," and "non-senescent cell" refer to a cell with an enhanced ability to proliferate, a decrease in lipofuscin accumulation, a decrease in the activity of β-galactosidase, a decrease in mitochondrial reactive oxygen species, an increase in mitochondrial membrane potential, and/or a decrease in duration of G0 and/or G1 phase of the cell occurs, when compared to a reference cell (e.g., a known senescent cell of the same type). The term "reference cell" refers to a cell, for example, a fibroblast derived from a person aged 18 to 25, 18 to 23, or 18 to 20 who are normal and healthy. The reference cell may be a fibroblast cell, a muscle cell, or nerve cell.

As used herein, the term "passage" refers to the subculturing of cells by the transfer of one or more cells growing in an existing cell culture into a new cell culture medium.

The composition may be combined with one or more other therapeutic agents for treating cell senescence-related diseases. In addition, the composition may only include a Rho-kinase inhibitor or a pharmaceutically acceptable salt or solvate thereof, without including another active ingredient for the treatment of the cell senescence-related diseases.

Provided is a method of reducing cell senescence in a mammal by administering an effective amount of a Rho-kinase inhibitor to the mammal.

In the method, the "Rho-kinase inhibitor," "reducing of cell senescence" and "mammal" are as described above. The "effective amount" refers to an amount sufficient to reduce cell senescence when administered to a subject having senescent cells (e.g., an increase in cellular proliferation or a reduction in accumulation of lipofuscin). The administering of the Rho-kinase inhibitor includes administering the composition including the Rho-kinase inhibitor or a pharmaceutically acceptable salt or solvate thereof.

Provided is a method of treating cell senescence-related symptoms by administering an effective amount of a Rho-kinase inhibitor to the mammal.

According to an aspect of another exemplary embodiment, provided is a method for treating a symptom associated with the accumulation of lipofuscin in a mammal, wherein said method includes: administering an effective amount of the Rho-kinase inhibitor to a mammal to treat the symptom associated with the accumulation of lipofuscin.

In the method, the "Rho-kinase inhibitor," "senescence-related symptoms," and "mammal" are as described above. The "effective amount" refers to an amount sufficient to treat cell senescence-related symptoms when administered to a subject having cell senescence-related symptoms (e.g., an increase in cellular proliferation or a reduction in accumulation of lipofuscin). The effective amount also refers to an amount sufficient enough to reduce the accumulation of lipofuscin when administered to a subject having the accumulation of lipofuscin. The accumulation of lipofuscin may be an accumulation of lipofuscin within a cell such as fibroblast, muscle cell such as myoblast, or nerve cell. The administering of the Rho-kinase inhibitor includes administering the composition including the Rho-kinase inhibitor or a pharmaceutically acceptable salt or solvate thereof.

In the methods described herein, the method may further include identifying a mammal with cellular senescent. The identifying step may include measuring the level of lipofuscin accumulation, activity of β-galactosidase, the number of mitochondrial reactive oxygen species (ROS), mitochondrial membrane potential, and the period of the G0 and/or G1 phase of the cell cycle. The measurement may conducted using a known method in the art. For example, the level of lipofuscin accumulation may be measured by using measuring the autofluorescence capability of a cell which is derived from a lipofuscin. Specifically, the cultured cells may be irradiated with a wavelength of 488 nm, and then measured with radiation emitted from a wavelength of 520 nm. The level of activity of β-galactosidase may measured by using a chromogenic substrate such as X-gal chromogenic substrate and detecting the light from the chromogenic substrate after reaction with sample containing the β-galactosidase. The level of the number of mitochondrial reactive oxygen species (ROS) may be measured by using a mitochondrial superoxide indicator such as 0.2 µM MitoSOX™ Red mitochondrial superoxide indicator for live-cell imaging (Invitrogen, M36008) and then, detecting a light emitted from the indicator after reaction with the mitochondrial reaction oxygen species. Cell cycle analysis e.g., the period of the G0 and/or G1 phase, S phase and G2/M phase may be achieved by monitoring DNA content. G0/G1-phase cells are diploid (2N) and express half the DNA content of tetraploid G2/M phase cells (4N). S phase cells contain varying amounts of DNA between the G1 and G2 states.

In the methods described herein, a route of administration may be selected by one of ordinary skill in the art in accordance with pathological conditions of a patient. The administration may be an oral, parenteral, or local administration. The administration may be local administration to tissues including senescent cells. The administration may be local administration to skin tissues, muscular tissues, or nervous tissues.

In the method, a dose may vary according to various factors such as pathological conditions of a patient as described above, a route of administration, and physician's decisions. An effective dose may be estimated based on dose-reaction curves obtained by in vitro experiments or animal model experiments. A ratio and concentration of the Rho-kinase inhibitors according to an exemplary embodiment contained in the composition may be determined according to chemical properties, a route of administration, a therapeutically effective dose, and the like. The dose administered to a subject may be in a range of about 10 µg/kg to about 10 g/kg per day, about 100 µg/kg to about 1 g/kg per day, about 1000 µg/kg to about 0.1 g/kg per day, about 10 µg/kg to about 1 g/kg per day, about 10 µg/kg to about 0.1 g/kg per day, about 10 µg/kg to about 0.01 g/kg per day, about 1 µg/kg to about 1 g/kg per day, or about 0.1 mg/kg to about 500 mg/kg per day, as an effective amount. The dose may be adjusted in accordance with age, weight, sensitivity, or symptoms of the subject.

The method may further include measuring the doubling time of a cell, the amount of lipofuscin in a cell, β-galactosidase activity in a cell, the number of mitochondrial ROS in a cell, mitochondrial membrane potential, and the period of the G0 and/or G1 phase of the cell cycle for a cell. The method may further include comparing the resultant data of the measurement with that of a control cell, wherein the control cell is a reference cell. The reference cell may a known non-senescent cell of the same cell type. The term "reference cell" refers to a cell, for example, a fibroblast derived from a person aged 18 to 25, 18 to 23, or 18 to 20 who are normal and healthy. The reference cell may be a fibroblast cell, a muscle cell such as myoblast, or nerve cell.

The method may further include determining that the cell is a senescent cell, when increased the doubling time of a cell, increased accumulation of lipofuscin in a cell, increased β-galactosidase activity in a cell, increased the number of mitochondrial ROS in a cell, decreased mitochondrial membrane potential, and increased the period of the G0 and/or G1 phase of the cell cycle for a cell is observed compared to the reference cell. The method may further include determining that the cell has an accumulation of lipofuscin, when increased amount of lipofuscin in a cell is observed compared to the reference cell.

In the method described above, the step of administering may conducted for/to the mammal who is determined to having a senescent tissue containing a senescent cell.

Provided is a method of treating an intracellular lipofuscin accumulation-related symptom in a mammal, wherein the method includes treating a lipofuscin accumulation-related symptom by administering an effective amount of a Rho-kinase inhibitor to the mammal.

In the method, the "Rho-kinase inhibitor," "senescence-related symptoms" and "mammal" are as described above. The "effective amount" refers to an amount sufficient to treat cell senescence-related symptoms when administered to a subject having cell senescence-related symptoms (e.g., an increase in cellular proliferation or a reduction in accumulation of lipofuscin). The administering of the Rho-kinase inhibitor includes administering the composition including the Rho-kinase inhibitor or a pharmaceutically acceptable salt or solvate thereof.

The composition including a Rho-kinase inhibitor or a pharmaceutically acceptable salt or solvate thereof may be used to reduce cell senescence.

According to a method of reducing cell senescence in mammals according to another exemplary embodiment, cell senescence may be efficiently reduced and cell senescence-related symptoms may be efficiently treated.

The method of treating a symptom associated with the accumulation of lipofuscin in a mammal according to another aspect may be used to treat the symptom associated with the accumulation of lipofuscin in a mammal.

Embodiments of the present invention will be described in further detail with reference to the following examples. These examples are for illustrative purposes only and are not intended to limit the scope of the invention.

EXAMPLES (1) Effect of Y-27632, Fasudil, and SR3677 on Proliferation of Senescent Fibroblast (after 37 Cell Passages)

Fibroblast cell lines were cultured in Dulbecco's Modified Eagle's Media (DMEM) supplemented with 10% fetal bovine serum (FBS) and 100 unit/ml of penicillin, and 100 µg/ml of streptomycin (two antibiotics are purchased from Gibro-BRL and Grand Island, N.Y.) in a 5% $CO_2$ incubator at 37° C. The fibroblast cell lines (M11 strain) were obtained from a foreskin of an 11-year-old boy. Subculture was initiated when the cells were approximately 85% confluent in plates. Early subcultures were performed at a split ratio of 1:4, and later subcultures were performed at a split ratio of 1:2. When cell doubling time was 14 days, the cells were regarded as senescent fibroblasts (passages 35 to 37).

In order to determine optimum concentrations of Rho-kinase inhibitors Y-27632 (Selleckchem, S1049, 50 mg 2HCl salt form), FASUDIL (Selleckchem, S1573, 500 mg HCl salt form), and SR3677 (Synkinase, SYN1083, 10 mg), the senescent fibroblasts (after 37 cell passages) were seeded on each well of a 6-well plate in a concentration of 2,000 cells/well, and the wells were treated with 1 µM, 5 µM, 10 µM, 20 µM, and 30 µM of Y-27632, 1 µM, 5 µM, 10 µM, and 30 µM of FASUDIL, and 0.01 µM, 0.05 µM, 0.1 µM, 0.5 µM, and 1 µM of SR3677. In addition, a negative control group was prepared in the same manner, except that dimethyl sulfoxide (DMSO) was used. The culture media supplemented with the Rho-kinase inhibitors were changed at every 4 days, and colonies were stained with a 0.05% crystal violet stain after 4 weeks.

FIG. 1 illustrates experimental results of identifying cell proliferation and cell colony formation according to concentrations of Rho-kinase inhibitors Y-27632, Fasudil, and SR3677.

A of FIG. 1 illustrates the experimental results of identifying cell proliferation and cell colony formation in accordance with the concentration of Y-27632. In "A" of FIG. 1, Y-27632 had the greatest therapeutic effects on cell proliferation and cell colony formation in the concentrations of 5 µM, 10 µM, and 20 µM. However, Y-27632 reduces cell proliferation and cell colony formation due to toxic effects at the concentration of 30 µM. The lowest 5 µM was selected and used in the following experiments as the concentration having therapeutic effects on cell proliferation and cell colony formation among the concentrations of 5 µM, 10 µM, and 20 µM. In A of FIG. 1, 0.05 (v/v) % of DMSO was used in the negative control group.

"B" of FIG. 1 illustrates the experimental results of identifying cell proliferation and cell colony formation in accordance with the concentration of FASUDIL. In B of FIG. 1, FASUDIL had the greatest therapeutic effects on cell proliferation and cell colony formation in the concentration of 5 µM. However, FASUDIL reduces cell proliferation and cell colony formation due to toxic effects at the concentrations of 10 µM, 20 µM, and 30 µM. 5 µM was selected and used in the following experiments as the concentration having therapeutic effects on cell proliferation and cell colony formation. In B of FIG. 1, 0.05 (v/v) % of DMSO was used in the negative control group.

"C" of FIG. 1 illustrates the experimental results of identifying cell proliferation and cell colony formation in accordance with the concentration of SR3677. In C of FIG. 1, SR3677 had the greatest therapeutic effects on cell proliferation and cell colony formation in the concentration of 0.5 µM. However, SR3677 reduces cell proliferation and cell colony formation due to toxic effects thereon in the concentration of 1 µM. 0.5 µM was selected and used in the following experiments as the concentration having therapeutic effects on cell proliferation and cell colony formation. In C of FIG. 1, 0.05 (v/v) % of DMSO was used in the negative control group.

In order to quantitatively measure the degree of cell proliferation induced by Y-27632, FASUDIL, and SR3677 in the optimum concentrations of 5 µM, 5 µM, and 0.5 µM, respectively, the cells were seeded on each well of a 96-well plate in a concentration of 2,000 cells/well. Then, 5 µM of Y-27632, 5 µM of FASUDIL, and 0.5 µM of SR3677 were added thereto, and the cells were cultured in the same conditions. In addition, the negative control group was prepared in the same manner, except that the DMSO instead of the ROCK inhibitor was used. The numbers of cells were counted using a Haematometer at $4^{th}$, $8^{th}$, $12^{th}$, and $16^{th}$ days to measure changes in the numbers of cells seeded on the 96-well plate.

Figure 2:
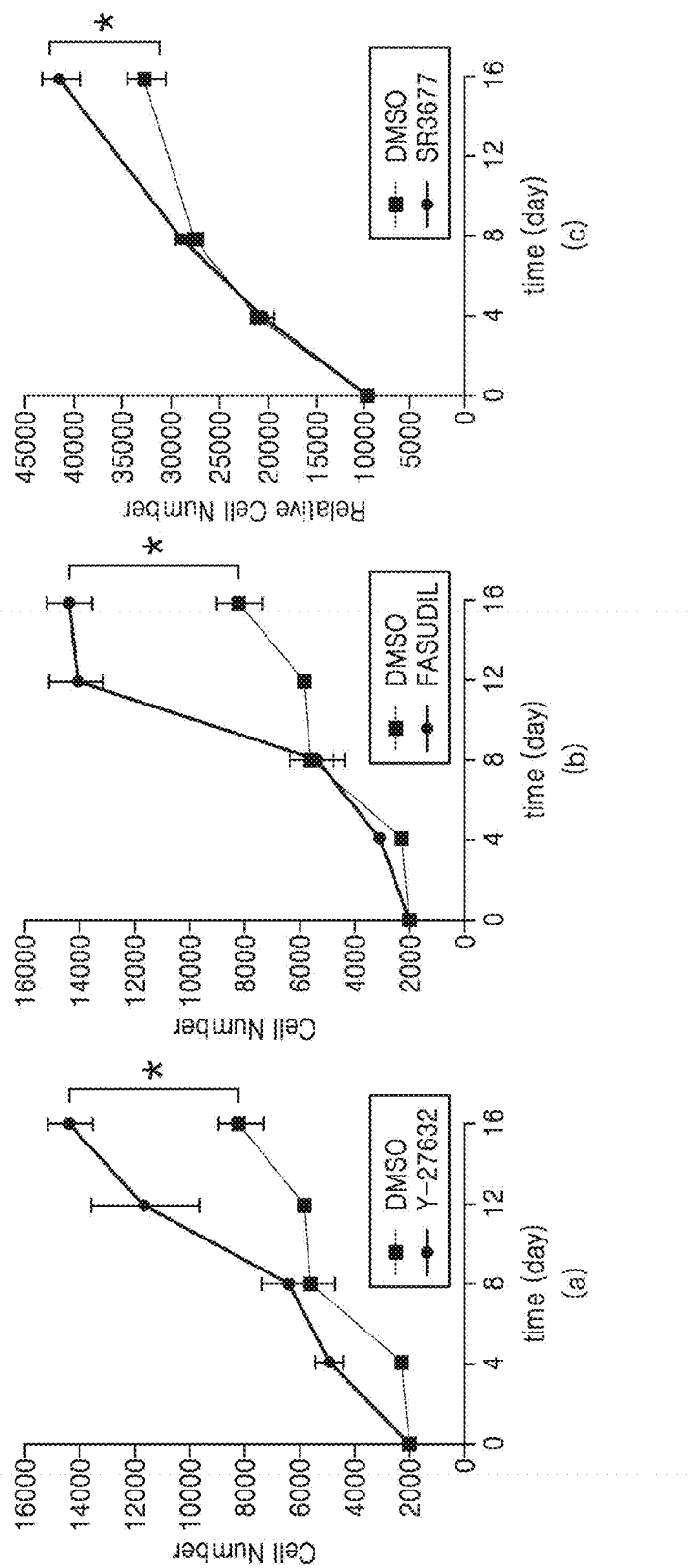
FIG. 2 is a series of graphs plotting relative cell number against time for senescent fibroblasts (after 37 cell passages) cultured in the presence of Rho-kinase inhibitors Y-27632 (5 µM), Fasudil (5 µM), and SR3677 (0.5 µM)

FIG. 2 illustrates graphs of the numbers of cells when senescent fibroblasts (after 37 cell passages) are cultured in the presence of Y-27632, FASUDIL and SR3677. Referring to FIG. 2, 5 µM of Y-27632, 5 µM of FASUDIL, and 0.5 µM of SR3677 were added to the cells and the cells were cultured in a 5% $CO_2$ incubator at 37° C. New culture media respectively supplemented with 5 µM of Y-27632, 5 µM of FASUDIL, and 0.5 µM of SR3677 were added to the cells every 4 days. In FIG. 2, data was determined from twelve replicates (n=12). As illustrated in FIG. 2, when cultured in the presence of these Rho-kinase inhibitors for 16 days, the numbers of cells were significantly increased compared with that of the negative control group (DMSO). In FIG. 2, * indicates statistically significant (p<0.05). In FIG. 2, 0.05 (v/v) % of DMSO was added to the culture medium in the negative control group.

Figure 3:
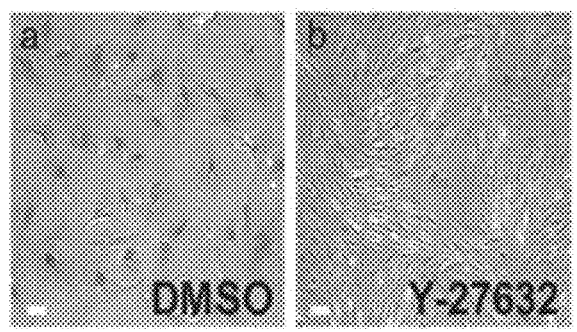
FIG. 3 is a microscopic image illustrating cell shapes of senescent fibroblasts (after 37 cell passages) cultured in the presence of Rho-kinase inhibitor Y-27632 (5 µM)

In addition, after senescent fibroblasts (after 37 cell passages) were cultured in the same culture media and same conditions as described above in the presence of 0.05 (v/v) % of DMSO and Y-27632 (5 µM), shapes of the cells were observed using a microscope. FIG. 3 is a microscopic image illustrating cell shapes of senescent fibroblasts (after 37 cell passages) cultured in the presence of Y-27632 for 4 weeks. As illustrated in FIG. 3, the numbers of cells cultured in the presence of Y-27632 (b) were greater than that of the control group (DMSO, a), and the cells cultured in the presence of Y-27632 (b) had a spindle shape generally found in young cells (Scale bar 20 µm).

The senescent fibroblasts (after 37 cell passages) were cultured in culture media respectively supplemented with 5 µM of Y-27632 (A), 5 µM of FASUDIL (B), and 0.5 µM of SR3677 (C) for 4 weeks in a 5% $CO_2$ incubator at 37° C. The culture media were changed with new culture media respectively supplemented with 5 µM of Y-27632, 5 µM of FASUDIL, and 0.5 µM of SR3677 at every 4 days. Cell cycles were measured using a Muse™ Cell Cycle Kit (MERCK Millipore, MCH100106) in accordance with manufacturer's manuals. Light having a wavelength of 488 nm was irradiated to the cells using a Muse™ Cell Analyzer (MERCK Millipore) and light emission at 520 nm was measured. The results were analyzed using Cell Quest 3.2 software (Beckton Dickinson). The control group was prepared in the same manner, except that 0.05 (v/v) % of DMSO was added thereto.

Figure 4:
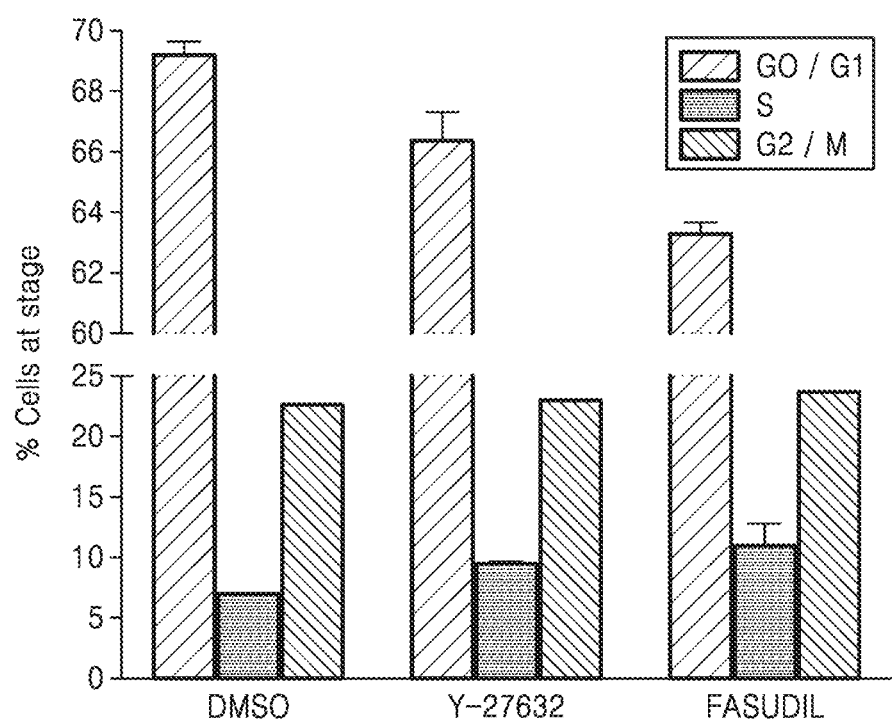
FIG. 4 is a graph of the percentage of cells at various cell growth stages illustrating the effects of Rho-kinase inhibitors Y-27632 and Fasudil on cell cycle of senescent fibroblasts (after 37 cell passages)

FIG. 4 is a graph displaying effects of Y-27632 and FASUDIL on cell cycle of senescent fibroblasts (after 37 cell passages). As illustrated in FIG. 4, the number of cells in G0/G1 phases was less than that of cells in S and G2/M phases in the presence of Y-27632 and FASUDIL when compared to the control group. This is because, in the presence of Y-27632 and FASUDIL, the cell cycle enters the S and G2/M phases enabling cell proliferation, thereby enhancing the ability of the cells to proliferate.

In addition, a soft agar assay was performed in order to identify whether the cells proliferated by the culturing are involved in abnormal proliferation such as cancer cell proliferation. First, a DMEM supplemented with 10% FBS was mixed with 1.6% agar in a ratio of 1:1 to prepare an agar solution having a concentration of 0.8%, and the agar solution was added to a 6-well plate. 2,500 cells were added to culture media respectively supplemented with 5 µM of Y-27632, 5 µM of FASUDIL, and 0.5 µM of SR3677, and the mixtures of the cells and the culture media were mixed with the 0.8% agar solution to an agar concentration of 0.4. Then, the final mixture was spread on the 0.8% agar solution applied on the well plate. The cells were cultured in a 5% $CO_2$ incubator at 37° C. for 4 weeks. The culture media respectively supplemented with 5 µM of Y-27632, 5 µM of FASUDIL, and 0.5 µM of SR3677 were added thereto at every 4 days to prevent the agar from drying. As a control group, Human Embryonic Kidney 293T cell lines (ATCC® CRL-11268™) were used. In addition, a negative control group was prepared in the same manner, except that 0.05 (v/v) % of DMSO was used.

Figure 5:
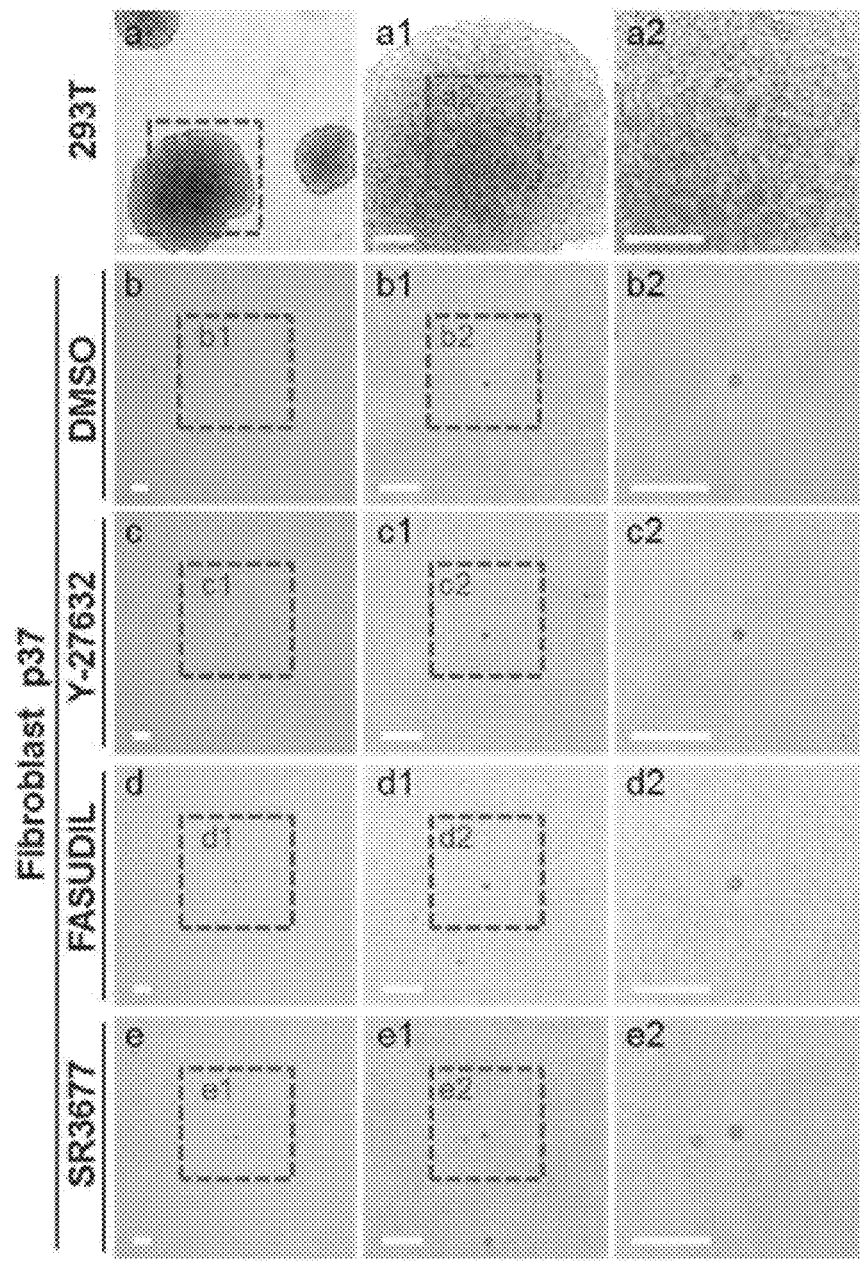
FIG. 5 is a diagram of microscopic images illustrating the results of culturing senescent fibroblasts (after 37 cell passages) in the presence of Rho-kinase inhibitors Y-27632 (5 µM), Fasudil (5 µM), and SR3677 (0.5 µM), in agar-containing culture media.

FIG. 5 is a diagram illustrating results of culturing fibroblasts (after 37 cell passages), cultured in culture media in the presence of Rho-kinase inhibitors, in agar-containing culture media. As illustrated in FIG. 5, although 293T cells, which are cancer cells, formed colonies, the other cells did not form colonies. In "a" of FIG. 5, a portion was selected, marked by a rectangle with a dashed line, and enlarged in a1 for closer examination of colonies. In a1 of FIG. 5, a portion was selected, marked by a rectangle with a dashed line, and enlarged in a2 for much closer examination of colonies (Scale bar 20 µm). In FIG. 5, Fibroblast 37 refers to fibroblasts subcultured for 37 passages.

(2) Effect of Y-27632, FASUDIL, and SR3677 on Restoration of Senescent Fibroblast (after 37 Cell Passages) to a Young Cell Effects of Rho-kinase inhibitors on expression of senescence-associated β-galactosidase (SA-β-gal) were identified by treating the proliferated cells with a β-galactosidase staining kit (Cell Signaling Technology, #9860, Beverly, Mass.). A chromogenic substrate (X-gal) having a pH of 6.0 was incubated overnight at 37° C. according to manufacturer's protocols.

Figure 6A:
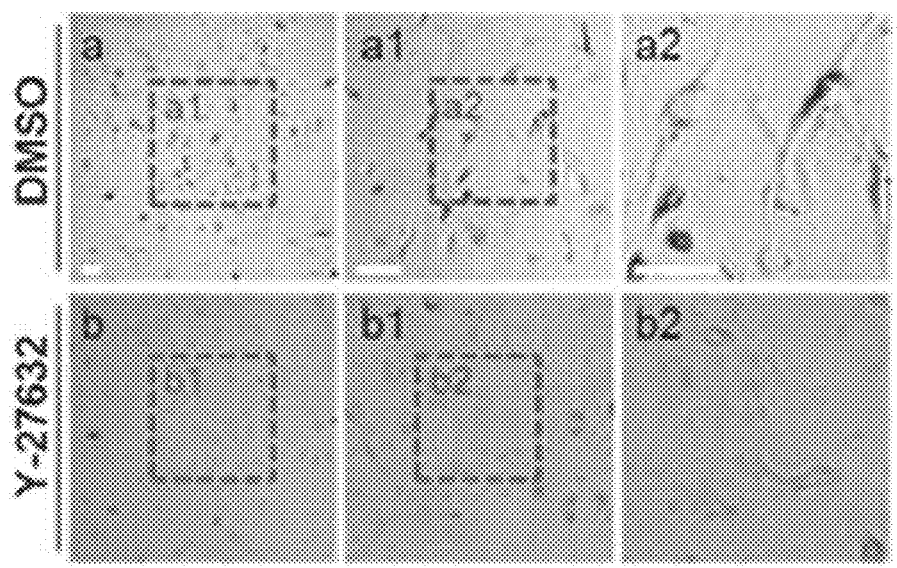
FIGS. 6A, 6B, 7A, 7B, 8A, and 8B are diagrams of microscopic images illustrating senescence associated (SA)-β-galactosidase activities (panels (a) and (b) of FIGS. 6A, 7A, and 8A) of senescent fibroblasts (after 37 cell passages) cultured in the presence of Rho-kinase inhibitors Y-27632 (5 µM), Fasudil (5 µM), and SR3677 (0.5 µM), and graphs illustrating senescence percentages of cells with senescence associated (SA)β-galactosidase activities (FIGS. 6B, 7B, and 8B)
Figure 6B:
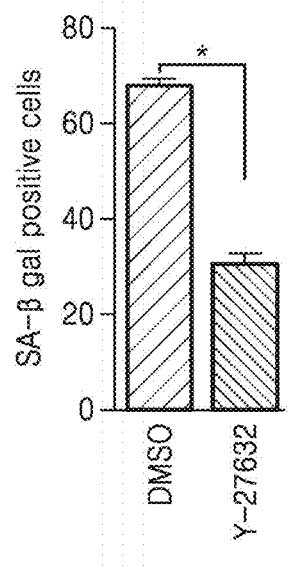
Figure 7A:
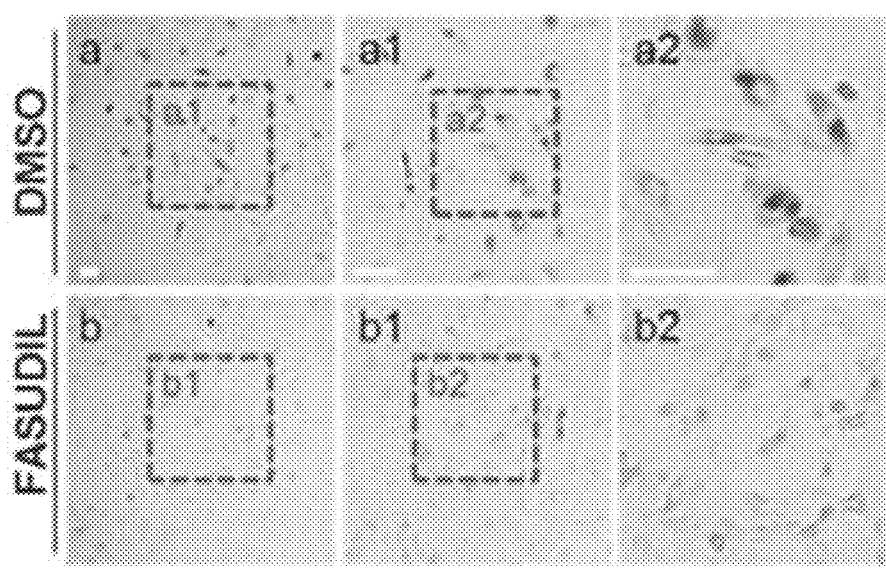
Figure 7B:
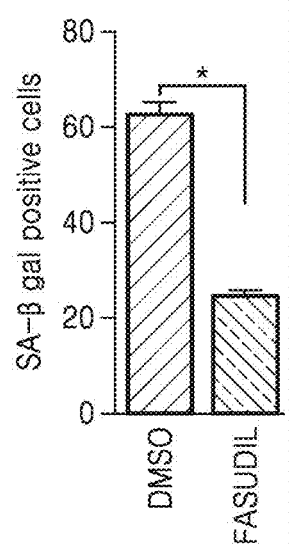
Figure 8A:
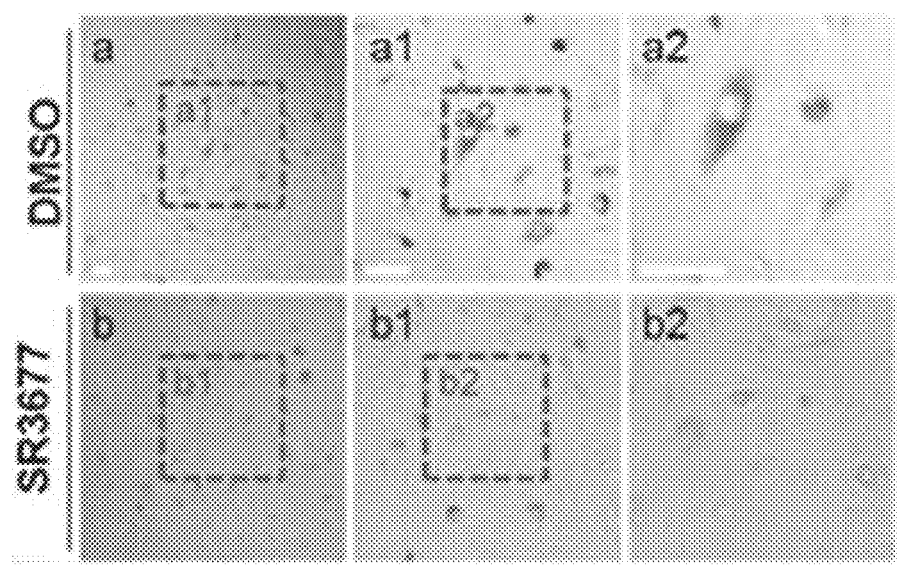
Figure 8B:
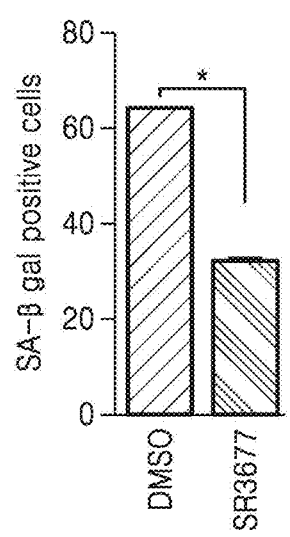

FIGS. 6A, 6B, 7A, 7B, 8A, and 8B are diagrams illustrating SA-β-galactosidase activities (a and b) of fibroblasts (after 37 cell passages) cultured in the presence of Y-27632 (5 µM), Fasudil (5 µM), and SR3677 (0.5 µM), and graphs illustrating percentages of cells with the activities (FIGS. 6B, 7B, and 8B). In FIG. 6A, a, a1, and a2 show negative control groups using DMSO, and b, b1, and b2 show cells treated with 5 µM of Y-27632. In "a", a portion of was selected, marked by a rectangle with a dashed line, and enlarged in a1 for closer examination of stained cells. In a1, a portion was selected, marked by a rectangle with a dashed line, and enlarged in a2 for closer examination of colonies (Scale bar 20 µm).

As illustrated in FIGS. 6B, 7B, and 8B, in the presence of the Rho-kinase inhibitors, the number of cells in which β-galactosidase was expressed was significantly reduced when compared to the control group (treated with 0.05 (v/v) % of DMSO). In FIGS. 6B, 7B, and 8B, * indicates statistically significant (p<0.05).

Figure 9:
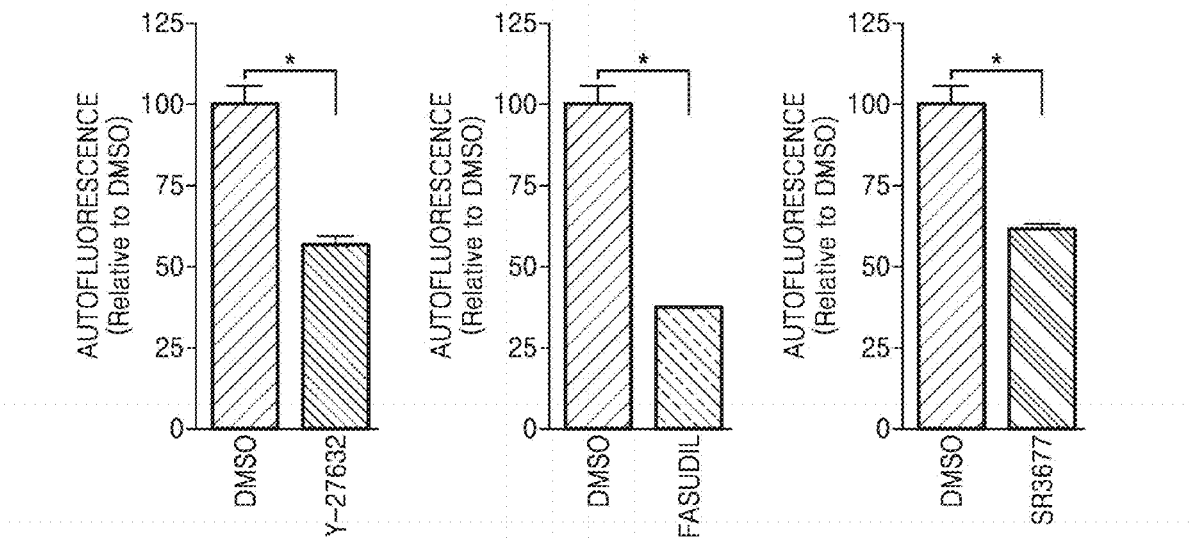
FIG. 9 is a set of graphs displaying amounts of lipofuscin in fibroblasts (after 37 cell passages) cultured in the presence of Rho-kinase inhibitors Y-27632 (5 µM), Fasudil (5 µM), and SR3677 (0.5 µM)

In addition, amounts of lipofuscin accumulated in the cultured cells were measured. Senescent cells (After 37 cell passages) were cultured for 4 weeks in a 5% $CO_2$ incubator at 37° C. in the presence of 5 µM of Y-27632, 5 µM of FASUDIL, and 0.5 µM of SR3677. The culture media were changed at every 4 days with new culture media supplemented with 5 µM of Y-27632, 5 µM of FASUDIL, and 0.5 µM of SR3677. Since lipofuscin has autofluorescence characteristics, light having a wavelength of 488 nm was irradiated to the cells by using a FACSCaliber (Beckton Dickinson) and light emission at 520 nm was measured. The results are analyzed using a Cell Quest 3.2 software (Beckton Dickinson). FIG. 9 is a graph displaying amounts of lipofuscin in fibroblasts (after 37 cell passages) cultured in the presence of Rho-kinase inhibitors Y-27632 (5 µM), Fasudil (5 µM), and SR3677 (0.5 µM). As illustrated in FIG. 9, in the presence of Y-27632, FASUDIL, and SR3677, the amounts of lipofuscin in cells were significantly reduced when compared to the control group. In FIG. 9, * indicates statistically significant (p<0.05).

Figure 10:
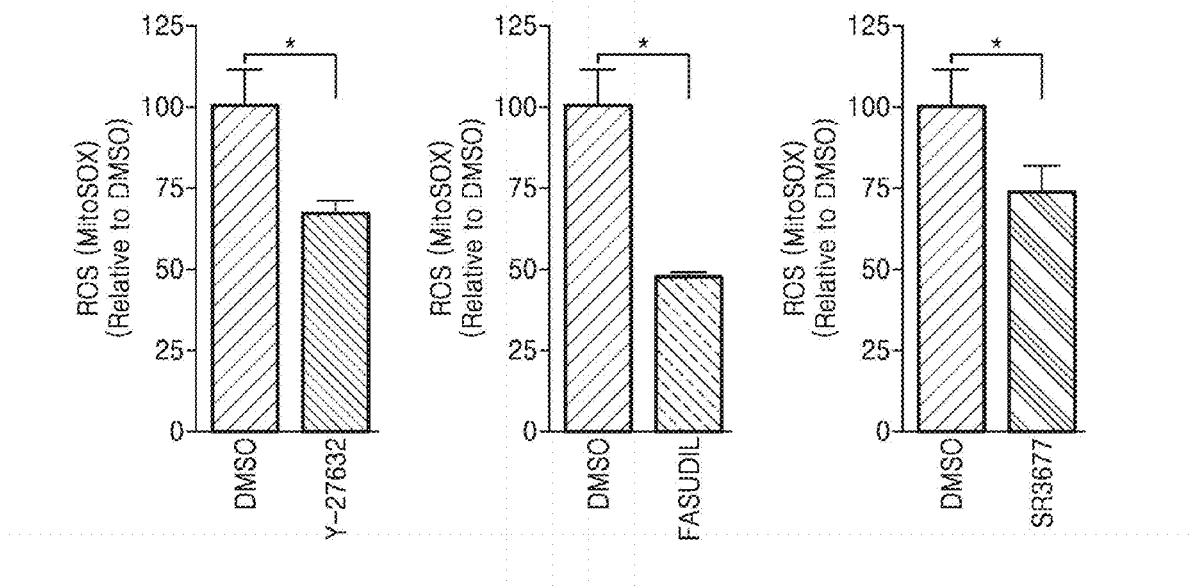
FIG. 10 is a set of graphs displaying reactive oxygen species in fibroblasts (after 37 cell passages) cultured in the presence of Rho-kinase inhibitors Y-27632 (5 µM), Fasudil (5 µM), and SR3677 (0.5 µM)

In addition, damage of mitochondria was identified by measuring reactive oxygen species (ROS) and mitochondrial membrane potentials which are well known in the art. ROS were measured using a 0.2 µM MitoSOX (Invitrogen, M3608) according to manufacturer's manuals. Light having a wavelength of 520 nm was irradiated to the cells using a FACSCaliber (Beckton Dickinson), and light emission was measured at 580 nm. The results were analyzed using a Cell Quest 3.2 software (Beckton Dickinson). As illustrated in FIG. 10, when compared to the control group, in the presence of Y-27632, FASUDIL and SR3677, ROS were significantly reduced in the cells. In FIG. 10, * indicates statistically significant (p<0.05).

Figure 11:
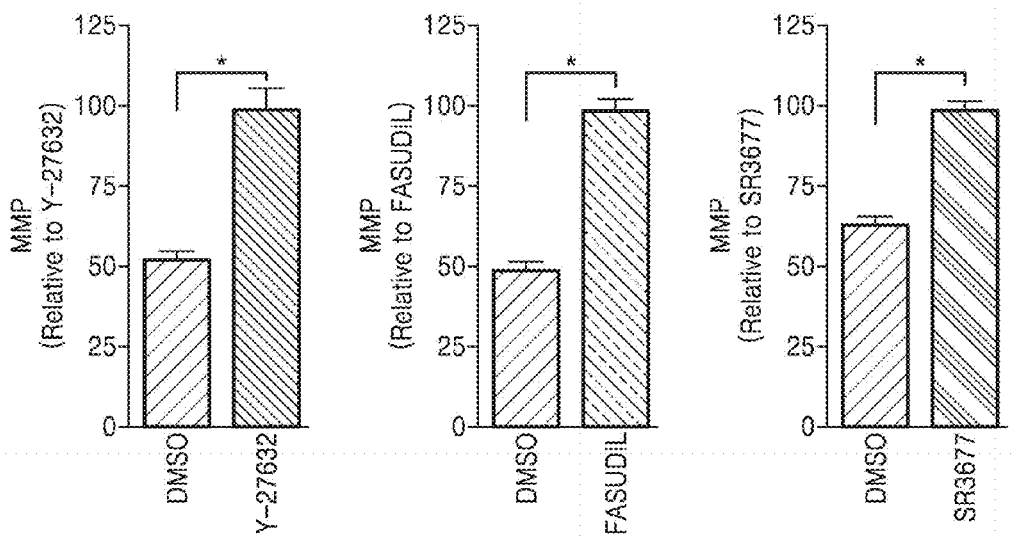
FIG. 11 is a set of graphs displaying mitochondrial membrane potentials of fibroblasts (after 37 cell passages) cultured in the presence of Rho-kinase inhibitors Y-27632 (5 µM), Fasudil (5 µM), and SR3677 (0.5 µM)

Mitochondrial membrane potentials were measured using a MitoProbe™ JC-1 Assay kit for Flow Cytometry (Life technologies, T3168) according to manufacturer's manuals. JC-1 is accumulated in mitochondria in a potential-dependent manner, and this accumulation is identified by fluorescence emission shift from green (about 529 nm) to red (about 590 nm). As a result, mitochondrial depolarization is identified by a decrease in a red/green fluorescence ratio. The mitochondrial membrane potentials were measured by excitation at 488 nm using a FACSCaliber (Beckton Dickinson) and using a flow cytometer by using 530/30 nm and 585/42 nm band pass filters. The results were analyzed using Cell Quest 3.2 software (Beckton Dickinson). FIG. 11 is a graph displaying action potentials of mitochondria. As illustrated in FIG. 11, the action potentials of mitochondria were significantly increased in the presence of Y-27632, FASUDIL, and SR3677 when compared to the control group. In FIG. 11, * indicates statistically significant (p<0.05). In FIG. 11, the vertical axis is mitochondrial membrane potential. "MMP" refers to mitochondria membrane potential.

Referring to FIGS. 10 and 11, it is confirmed that the activity of mitochondria was enhanced in the presence of Y-27632, FASUDIL, and SR3677.

The degrees of restoration of DNA damage in senescent cells by the Rho-kinase inhibitors were identified by a DNA comet assay. This method is performed by detecting DNA fractions cleaved by ultraviolet (UV) irradiation. This method is based on gel electrophoresis. During gel electrophoresis, damaged DNA migrates farther than normal DNA forming a tail like a comet-tail. Then, a slide was stained with SYBR Green, and the length of a tail of a DNA fraction was measured using a fluorescence microscope to identify the degree of DNA damage.

Figure 12:
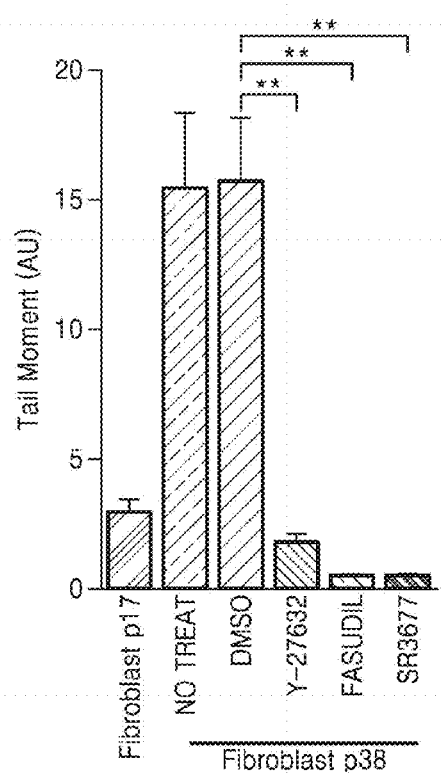
FIG. 12 is a graph displaying degrees of DNA damage in fibroblasts (after 38 cell passages) cultured in the presence of Rho-kinase inhibitors Y-27632 (5 µM), Fasudil (5 µM), and SR3677 (0.5 µM) measured by a DNA comet assay indicating the degree of DNA damage.

FIG. 12 is a graph displaying degrees of DNA damage in fibroblasts (after 38 cell passages) cultured in the presence of Rho-kinase inhibitors Y-27632 (5 µM), Fasudil (5 µM), and SR3677 (0.5 µM) measured by a DNA comet assay indicating the degree of DNA damage. In FIG. 12, senescent cells (after 38 cell passages) were cultured in culture media supplemented with 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. Also, negative control groups were prepared in the same manner as described above, except that one negative control group was prepared with no treatment and another was treated with 0.05 (v/v) % of DMSO. Cells having undergone 17 passages and having a cell doubling time of 4 to 5 days were used as young cells. As illustrated in FIG. 12, while a Tail Moment was shorter in the young cells, a Tail Moment increased in the senescent cells of the negative control group. Thus, it was confirmed that the degree of DNA damage increases in senescent cells. In the Comet assay, the Tail Moment is defined as multiplication of a length of the tail by a total DNA fraction contained in the tail. That is, the Tail Moment is a length of the tail migrated during gel electrophoresis. As the length of the tail decreases, the degree of DNA damage decreases. However, when compared to the control group, the DNA damage was considerably restored in the cells cultured in the presence of Y-27632, FASUDIL and SR3677, and the cells were restored to young cells. In FIG. 12,  indicates statistically significant (p<0.01). In FIG. 12**, the "Fibroblast p17" and "Fibroblast p38" refer to fibroblasts that were subcultured for 17 passages and fibroblasts subcultured for 38 passages, respectively.

(3) Effect of Y-27632, FASUDIL, and SR3677 on Restoration of Senescent Myoblast

Myoblast cell lines (Human Skeletal Muscle Myoblasts, Lonza CC-2580 LOT:0000387550) were cultured in SkBM™-2 Basal Media (Lonza CC-3246) including an SkGM™-2 SingleQuots™ Kit (Lonza CC-3244) on plates coated with Collagen Type I (Greiner Bio One, 658950) in a 5% $CO_2$ incubator at 37° C. Subculture was initiated when the cells were approximately 85% confluent in plates. Early subcultures were performed at a split ratio of 1:4, and later subcultures were performed at a split ratio of 1:2. When cell doubling time was 14 days, the cells were regarded as senescent myoblasts (cell passages 10 to 12).

Senescent cells were seeded on each well of a 6-well plate coated with Collagen Type I (Greiner Bio One, 657950) in a concentration of 2,000 cells/well. Senescent myoblasts (passage 11) were cultured in the presence of 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. A negative control group was prepared in the same manner, except that 0.05 (v/v) % of DMSO was used.

Figure 13:
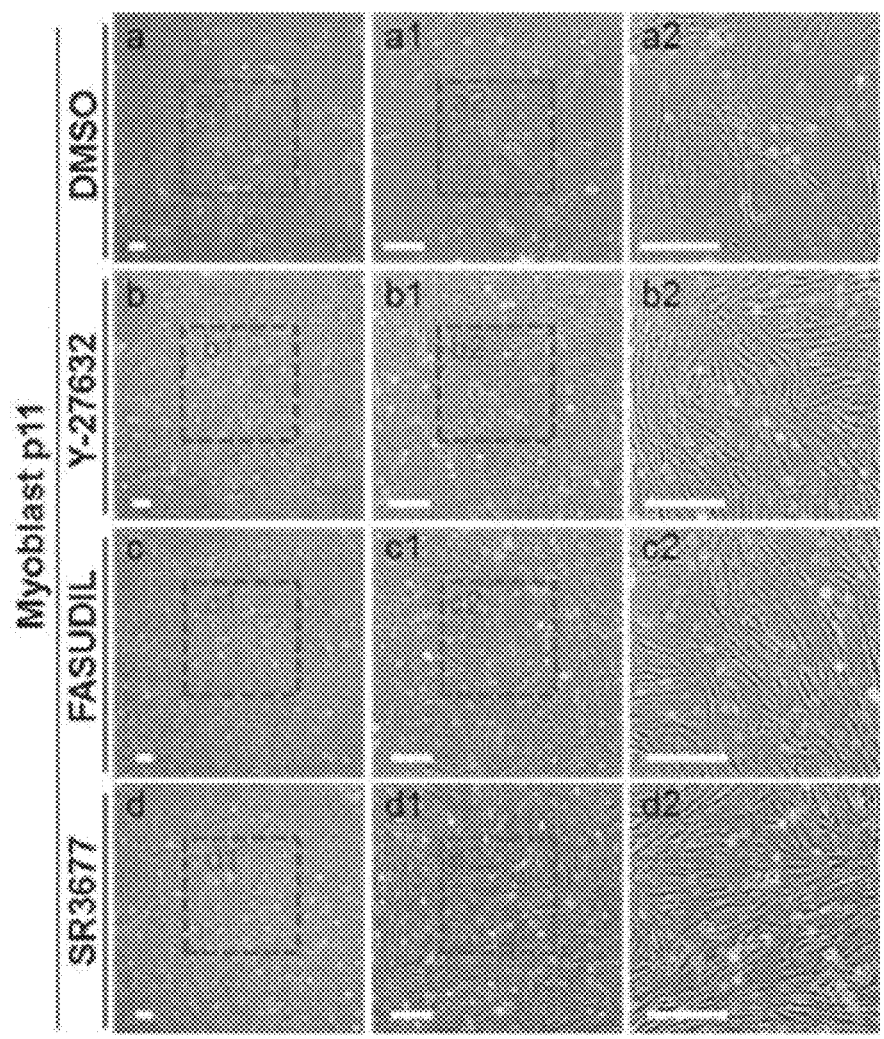
FIG. 13 is a diagram of microscopic images illustrating cell shape changes in myoblasts (after 11 cell passages) cultured in the presence of Rho-kinase inhibitors Y-27632 (5 µM), Fasudil (5 µM), and SR3677 (0.5 µM)

FIG. 13 is a diagram illustrating cell shape changes in myoblasts (passage 11) cultured in the presence of Rho-kinase inhibitors Y-27632 (5 µM), Fasudil (5 µM), and SR3677 (0.5 µM).

FIG. 13 illustrates microscopic images of cells cultured in the presence of 5 µM of Y-27632, 5 µM of FASUDIL, and 0.5 µM of SR3677. In "a" of FIG. 13, a portion was selected and marked by a rectangle with a dashed line, and the selected portion was enlarged in a1 for closer examination of the cultured cells. In a1 of FIG. 13, a portion was selected, marked by a rectangle with a dashed line, enlarged in a2 for much closer examination of the cultured cells (Scale bar 20 µm). As illustrated in FIG. 13, the numbers of cells cultured in the presence of Y-27632, FASUDIL, and SR3677 were greater than that of the control group (DMSO), and the cells cultured in the presence of Y-27632, FASUDIL, and SR3677 had a spindle shape generally found in young cells (Scale bar 20 µm).

Figure 14:
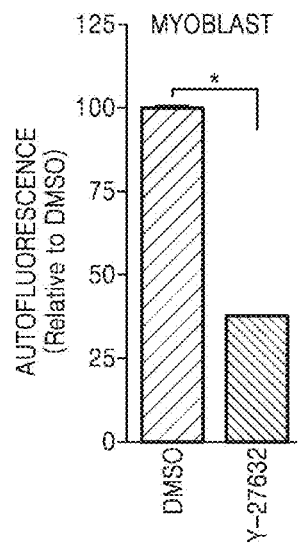
FIG. 14 is a set of graphs displaying amounts of lipofuscin in myoblasts (after 11 cell passages) cultured in the presence of Rho-kinase inhibitors Y-27632 (5 µM), Fasudil (5 µM), and SR3677 (0.5 µM)
Figure 14:
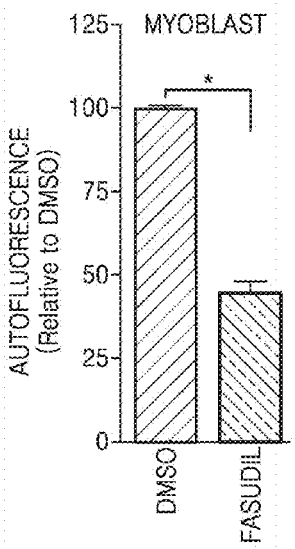
Figure 14:
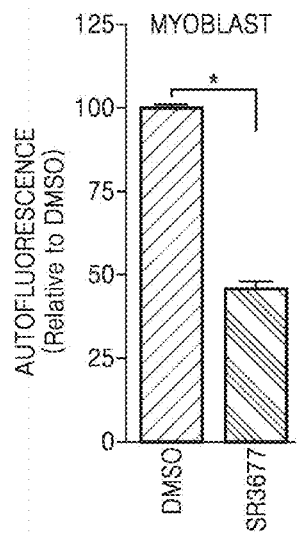

In addition, amounts of lipofuscin accumulated in the cultured cells were measured. Senescent myoblasts (11 cell passages) were cultured in the presence of 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. Since lipofuscin has autofluorescence characteristics, light having a wavelength of 488 nm was irradiated to the cells by using a FACSCaliber (Beckton Dickinson) and light emission at 520 nm was measured. The results were analyzed using Cell Quest 3.2 software (Beckton Dickinson). FIG. 14 is a graph displaying amounts of lipofuscin in myoblasts (11 cell passages) cultured in the presence of Rho-kinase inhibitors Y-27632 (5 µM), Fasudil (5 µM), and SR3677 (0.5 µM). As illustrated in FIG. 14, when compared to the control group, the amounts of lipofuscin were significantly reduced in the cells cultured in the presence of Y-27632, FASUDIL and SR3677. In FIG. 14, * indicates statistically significant (p<0.05).

In addition, the damage of mitochondria was identified by measuring reactive oxygen species (ROS) and mitochondrial membrane potentials which are well known in the art.

ROS were measured using a 0.2 µM MitoSOX (Invitrogen, M3608) according to manufacturer's manuals. Light having a wavelength of 520 nm was irradiated to the cells using a FACSCaliber (Beckton Dickinson), and light emission was measured at 580 nm. The results were analyzed using Cell Quest 3.2 software (Beckton Dickinson).

Figure 15:
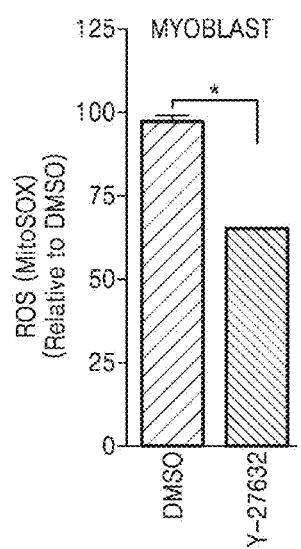
FIG. 15 is a set of graphs displaying reactive oxygen species in myoblasts (after 11 cell passages) cultured in the presence of Rho-kinase inhibitors Y-27632 (5 µM), Fasudil (5 µM), and SR3677 (0.5 µM)
Figure 15:
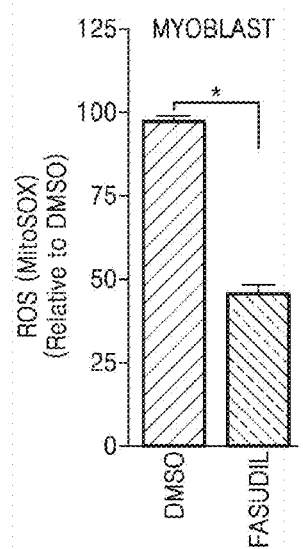
Figure 15:
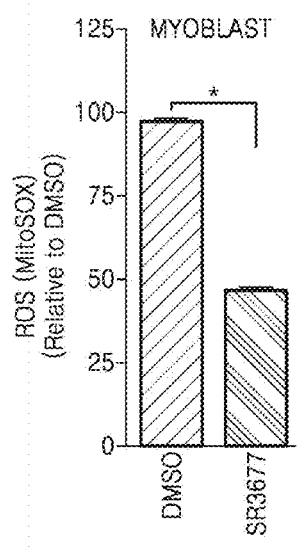

FIG. 15 is a graph displaying reactive oxygen species in myoblasts (11 cell passages) cultured in the presence of Rho-kinase inhibitors Y-27632 (5 µM), Fasudil (5 µM), and SR3677 (0.5 µM). As illustrated in FIG. 15, when compared to the control group, ROS were significantly reduced in the cells cultured in the presence of Y-27632, FASUDIL and SR3677. In FIG. 15, * indicates statistically significant (p<0.05).

Mitochondrial membrane potentials were measured using a MitoProbe™ JC-1 Assay kit for Flow Cytometry (Life technologies, T3168) according to manufacturer's manuals. JC-1 is accumulated in mitochondria in a potential-dependent manner, and this accumulation is identified by fluorescence emission shift from green (about 529 nm) to red (about 590 nm). As a result, mitochondrial depolarization is identified by a decrease in a red/green fluorescence ratio. The mitochondrial membrane potentials were measured by excitation at 488 nm using a FACSCaliber (Beckton Dickinson) and using a flow cytometer by using 530/30 nm and 585/42 nm band pass filters. The results were analyzed using Cell Quest 3.2 software (Beckton Dickinson).

Figure 16:
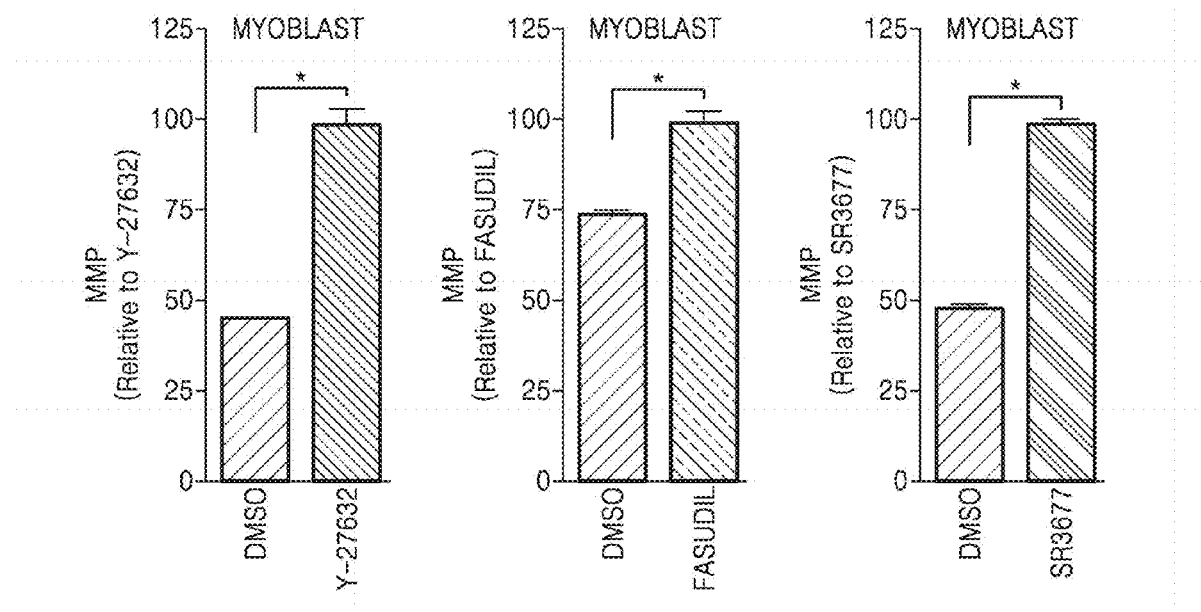
FIG. 16 is a set of graphs displaying mitochondrial membrane potentials of myoblasts (after 11 cell passages) cultured in the presence of Rho-kinase inhibitors Y-27632 (5 µM), Fasudil (5 µM), and SR3677 (0.5 µM)

FIG. 16 is a graph displaying action potentials of mitochondria. As illustrated in FIG. 16, the action potentials of mitochondria were significantly increased in the presence of Y-27632, FASUDIL, and SR3677 when compared to the control group. In FIG. 16, * indicates statistically significant (p<0.05). Referring to FIGS. 15 and 16, it was confirmed that the activity of mitochondria was enhanced in the presence of Y-27632, FASUDIL and SR3677.

(4) Effect of Y-27632, FASUDIL, and SR3677 on Restoration of Senescent Progeric Cell Progeric fibroblasts (Hutchinson-Gilford Progeria Syndrome Skin Fibroblasts, Coriell Cell Repositories, AG03198 B) were cultured in Dulbecco's Modified Eagle's Media (DMEM) supplemented with 10% fetal bovine serpm (FBS) and 100 unit/ml of penicillin, and 100 µg/ml of streptomycin (two antibiotics are purchased from Gibro-BRL and Grand Island, N.Y.) in a 5% $CO_2$ incubator at 37° C. Subculturing was initiated when the cells were approximately 85% confluent in plates. Early subcultures were performed at a split ratio of 1:4, and later subcultures were performed at a split ratio of 1:2. When cell doubling time was 14 days, the cells were regarded as senescent progeric fibroblasts (cell passages 16 to 17).

The senescent progeric fibroblasts (cell passage 17) were seeded on each well of a 6-well plate in a concentration of 2,000 cells/well and cultured in the presence of 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. A negative control group was prepared in the same manner, except that 0.05 (v/v) % of DMSO was used.

Figure 17:
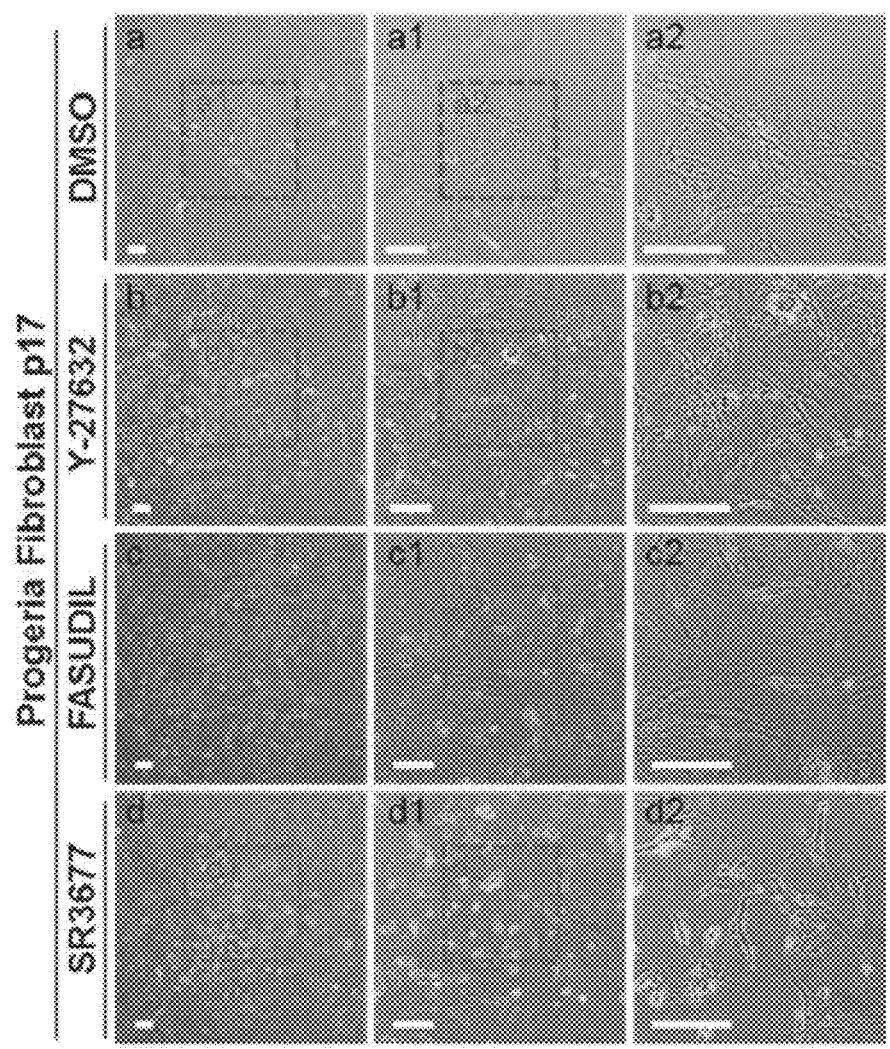
FIG. 17 is a diagram of microscopic images illustrating cell shape changes in progeric fibroblasts (after 17 passages) cultured in the presence of Rho-kinase inhibitors Y-27632 (5 µM), Fasudil (5 µM), and SR3677 (0.5 µM)

FIG. 17 is a diagram illustrating cell shape changes in progeric fibroblasts (passage 17) cultured in the presence of Rho-kinase inhibitors Y-27632 (5 µM), Fasudil (5 µM), and SR3677 (0.5 µM). In FIG. 17, the "Progeria Fibroblast p17" and "Progeria Fibroblast p11" refers to progeric fibroblasts subcultured for 17 cell passages and progeric fibroblasts subcultured for 11 cell passages, respectively.

FIG. 17 illustrates microscopic images of cells cultured in the presence of 5 µM of Y-27632, 5 µM of FASUDIL, and 0.5 µM of SR3677. In "a" of FIG. 17, a portion was selected, marked by a rectangle with a dashed line, and enlarged in a1 for closer examination of the cultured cells. In a1 of FIG. 17, a portion of a1 was selected, marked by a rectangle with a dashed line, and enlarged in a2 for much closer examination of the cultured cells (Scale bar 20 um). As illustrated in FIG. 17, the numbers of cells cultured in the presence of Y-27632, FASUDIL, and SR3677 were greater than that of the control group (DMSO), and the cells cultured in the presence of Y-27632, FASUDIL, and SR3677 had a spindle shape generally found in young cells (Scale bar 20 um).

Figure 18:
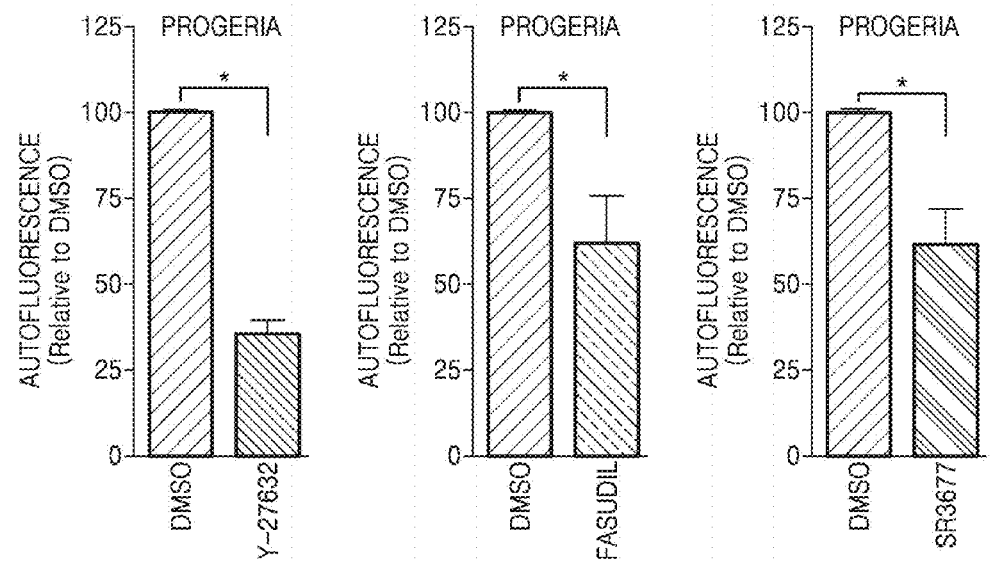
FIG. 18 is a set of graphs displaying amounts of lipofuscin in progeric fibroblasts (after 17 passages) cultured in the presence of Rho-kinase inhibitors Y-27632 (5 µM), Fasudil (5 µM), and SR3677 (0.5 µM)

In addition, the amounts of lipofuscin accumulated in the cultured cells were measured. Senescent progeric fibroblasts (passage 17) were cultured in the presence of 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. Since lipofuscin has autofluorescence characteristics, light having a wavelength of 488 nm was irradiated to the cells by using a FACSCaliber (Beckton Dickinson) and light emission at 520 nm was measured. The results were analyzed using Cell Quest 3.2 software (Beckton Dickinson). FIG. 18 is a graph displaying amounts of lipofuscin in progeric fibroblasts (passage 17) cultured in the presence of Rho-kinase inhibitors Y-27632 (5 µM), Fasudil (5 µM), and SR3677 (0.5 µM). As illustrated in FIG. 18, when compared to the control group, the amounts of lipofuscin were significantly reduced in the cells cultured in the presence of Y-27632, FASUDIL and SR3677. In FIG. 18, * indicates statistically significant ($p<0.05$).

Figure 19:
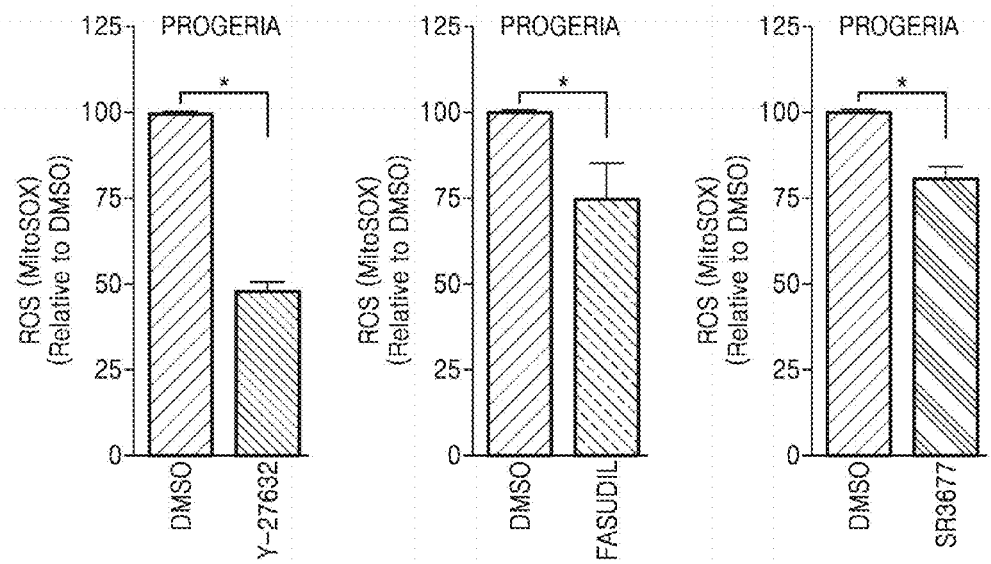
FIG. 19 is a set of graphs displaying reactive oxygen species in progeric fibroblasts (after 17 passages) cultured in the presence of Rho-kinase inhibitors Y-27632 (5 µM), Fasudil (5 µM), and SR3677 (0.5 µM)

In addition, damage of mitochondria was identified by measuring reactive oxygen species (ROS) and mitochondrial membrane potentials which are well known in the art. ROS were measured using a 0.2 µM MitoSOX (Invitrogen, M3608) according to manufacturer's manuals. Light having a wavelength of 520 nm was irradiated to the cells using a FACSCaliber (Beckton Dickinson), and light emission was measured at 580 nm. The results were analyzed using Cell Quest 3.2 software (Beckton Dickinson). FIG. 19 is a graph displaying reactive oxygen species of progeric fibroblasts (cell passage 17) cultured in the presence of Rho-kinase inhibitors Y-27632 (5 µM), Fasudil (5 µM), and SR3677 (0.5 µM). As illustrated in FIG. 19, when compared to the control group, ROS were significantly reduced in the cells cultured in the presence of Y-27632, FASUDIL and SR3677. In FIG. 19, * indicates statistically significant ($p<0.05$).

Figure 20:
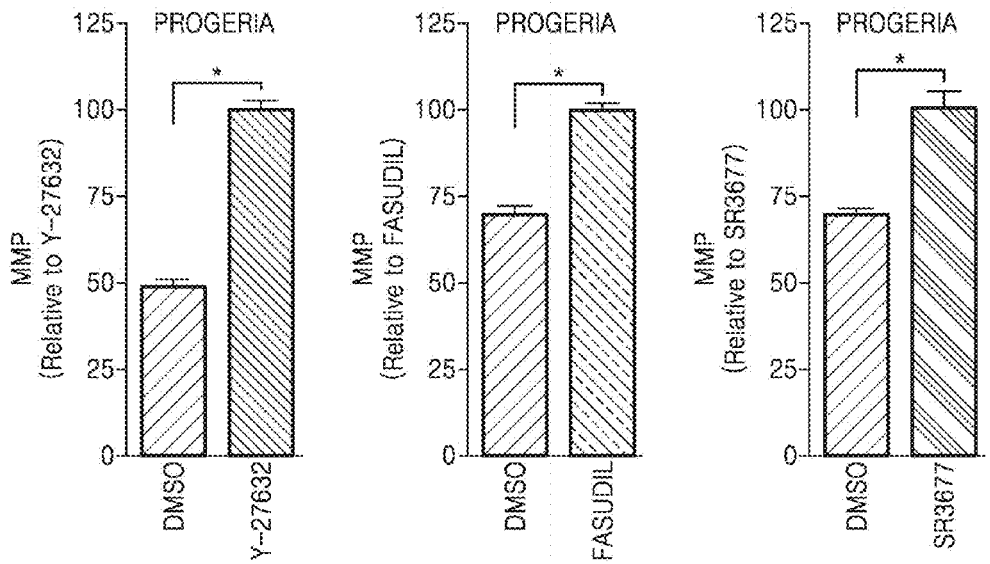
FIG. 20 is a set of graphs displaying mitochondrial membrane potentials of progeric fibroblasts (after 17 passages) cultured in the presence of Rho-kinase inhibitors Y-27632 (5 µM), Fasudil (5 µM), and SR3677 (0.5 µM)

Mitochondrial membrane potentials were measured using a MitoProbe™ JC-1 Assay kit for Flow Cytometry (Life technologies, T3168) according to manufacturer's manuals. JC-1 is accumulated in mitochondria in a potential-dependent manner, and this accumulation is identified by fluorescence emission shift from green (about 529 nm) to red (about 590 nm). As a result, mitochondrial depolarization is identified by a decrease in a red/green fluorescence ratio. The mitochondrial membrane potentials were measured by excitation at 488 nm using a FACSCaliber (Beckton Dickinson) and using a flow cytometer by using 530/30 nm and 585/42 nm band pass filters. The results were analyzed using Cell Quest 3.2 software (Beckton Dickinson). FIG. 20 is a graph displaying action potentials of mitochondria. As illustrated in FIG. 20, the action potentials of mitochondria were significantly increased in the presence of Y-27632, FASUDIL, and SR3677 when compared to the control group. In FIG. 20, * indicates statistically significant ($p<0.05$). Referring to FIGS. 19 and 20, it was confirmed that the activity of mitochondria was enhanced in the presence of Y-27632, FASUDIL and SR3677.

The degrees of restoration of DNA damage in senescent progeric fibroblasts by the Rho-kinase inhibitors were identified by a DNA comet assay. This method is performed by detecting DNA fractions cleaved by ultraviolet (UV) irradiation. This method is based on gel electrophoresis. During gel electrophoresis, damaged DNA migrates farther than normal DNA forming a tail like a comet-tail. Then, a slide was stained with SYBR Green, and the length of a tail of a DNA fraction was measured using a fluorescence microscope to identify the degree of DNA damage.

Figure 21:
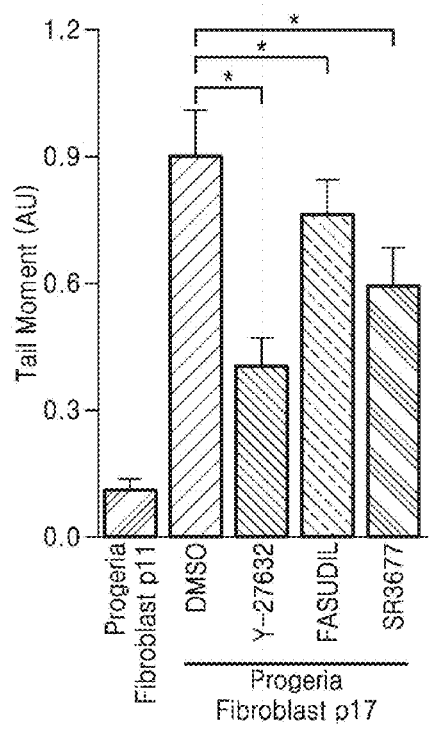
FIG. 21 is a graph displaying degrees of DNA damage in progeric fibroblasts (after 17 passages) cultured in the presence of Rho-kinase inhibitors Y-27632 (5 µM), Fasudil (5 µM), and SR3677 (0.5 µM) measured by a DNA comet assay indicating the degree of DNA damage.

FIG. 21 is a graph displaying degrees of DNA damage in progeric fibroblasts (cell passage 17) cultured in the presence of Rho-kinase inhibitors Y-27632 (5 µM), Fasudil (5 µM), and SR3677 (0.5 µM) measured by a DNA comet assay indicating the degree of DNA damage. In FIG. 21, senescent progeric cells (cell passage 17) were cultured in culture media supplemented with 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. Cells having a cell doubling time of 6 to 7 days were used as young cells. A negative control group was prepared in the same manner, except that DMSO was used. As illustrated in FIG. 21, while a Tail Moment was shorter in the young cells, a Tail Moment increased in the senescent cells of the negative control group (DMSO). Thus, it was confirmed that the degree of DNA damage increases in senescent cells. However, it was confirmed that when compared to the control group (DMSO), the DNA damage was considerably reduced in the cells cultured in the presence of Y-27632, FASUDIL and SR3677. In FIG. 21, * indicates statistically significant ($p<0.05$).

Effects of the Rho-kinase inhibitors on expression of senescence-associated β-galactosidase (SA-β-gal) were identified by treating the proliferated cells with a β-galactosidase staining kit (Cell Signaling Technology, #9860, Beverly, Mass.). A chromogenic substrate (X-gal) having a pH of 6.0 was incubated overnight at 37° C. according to manufacturer's protocols.

Figure 22A:
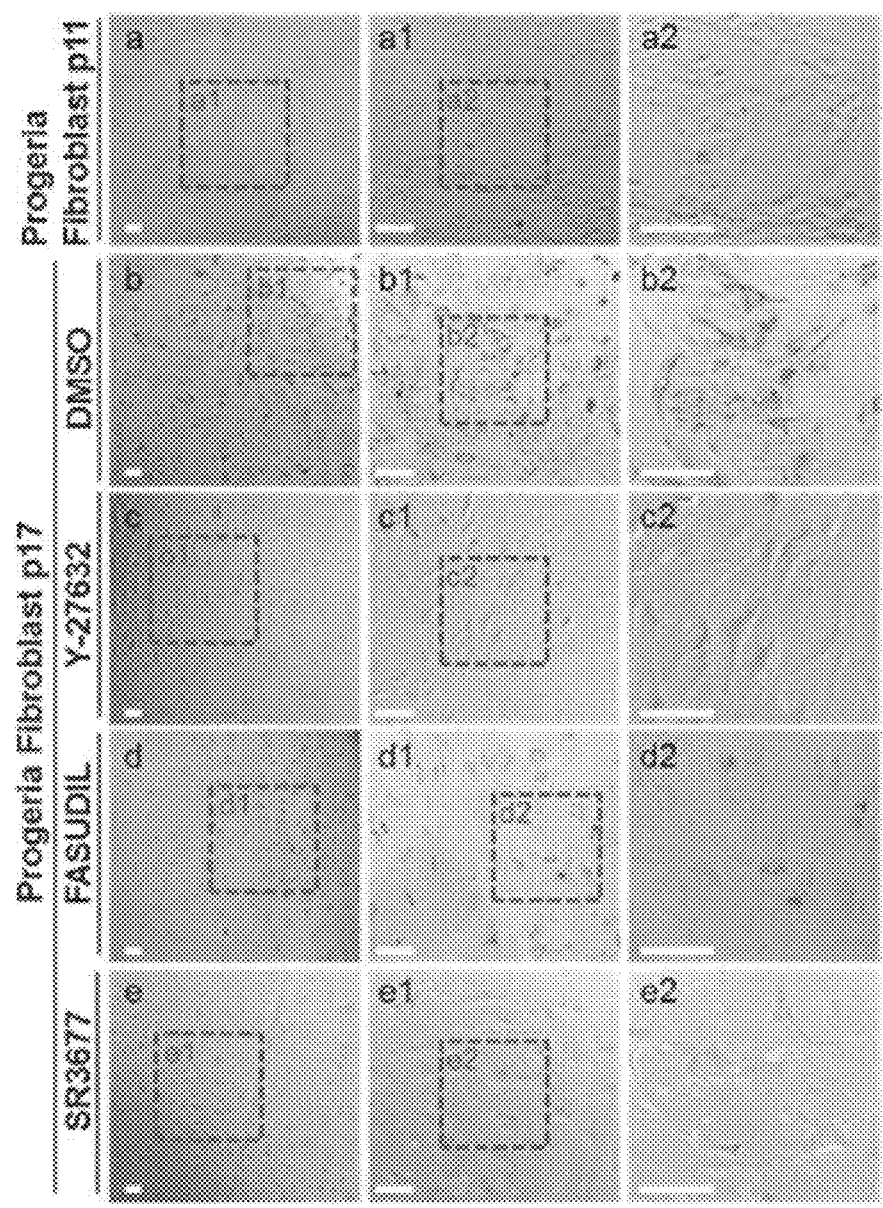
FIG. 22A is a diagram of microscopic images illustrating SA-β-galactosidase activities of progeric fibroblasts (after 17 passages) cultured in the presence of Rho-kinase inhibitors Y-27632 (5 µM), Fasudil (5 µM), and SR3677 (0.5 µM)
Figure 22B:
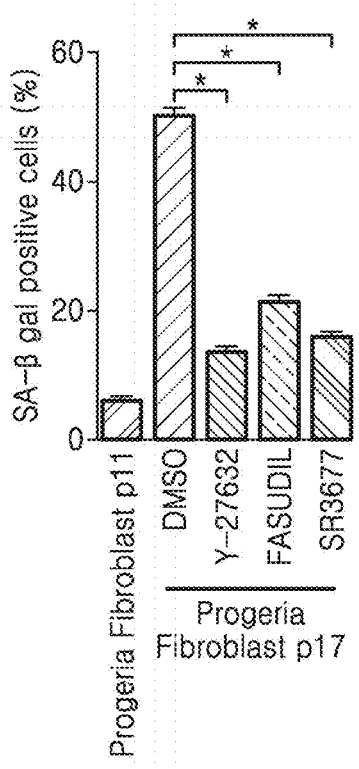
FIG. 22B is a graph displaying percentages of cells with the SA-β-galactosidase activities.

FIGS. 22A and 22B are a diagram illustrating SA-β-galactosidase activities (a, b, c, and d) of cells cultured in the presence of Y-27632 (5 µM), Fasudil (5 µM), and SR3677 (0.5 µM), and a graph displaying percentages of cells with the SA-β-galactosidase activities (f). In FIG. 22A, senescent progeric fibroblasts (cell passage 17) were cultured in the presence of 5 µM of Y-27632, 5 µM of FASUDIL, and 0.5 µM of SR3677 for 4 weeks in a 5% $CO_2$ incubator at 37° C. The culture media were changed at every 4 days with new culture media supplemented with 5 µM of Y-27632, 5 µM of FASUDIL, and 0.5 µM of SR3677. The cells that underwent 11 cell passages and having a cell doubling time of 6 to 7 days were used as young cells. In addition, a negative control group was prepared in the same manner, except the DMSO was used. In "a" of FIG. 22A, a portion was selected, marked by a rectangle with a dashed line, and enlarged in a1 for closer examination of stained cells. In a1 of FIG. 22, a portion was selected, marked by a rectangle with a dashed line, and enlarged in a2 for much closer examination of stained cells (Scale bar 20 µm). As illustrated in FIG. 22, although there is a few young cells in which β-galactosidase was expressed, the number of cells in which β-galactosidase was expressed significantly increased in the negative control group (DMSO). In the presence of the Rho-kinase inhibitors, the number of cells in which β-galactosidase was expressed significantly decreased when compared to the negative control group (DMSO). In FIG. 22B, * indicates statistically significant ($p<0.05$).

(5) In Vivo Effects of ROCK Inhibition on Wound Healing in Aged Mice (5.1) Materials and Methods
Wound Healing Assay, Immunohistochemistry, and Trichrome Staining To further test whether ROCK inhibitor can promote cutaneous wound healing in old (19 months old) male mice (C57BL/6J mice), four full-thickness punch-biopsy wounds (8 mm in diameter)(four wound sites/mouse, five mice/group) were created on the dorsal skin of mouse, 0.5 mL 10 µM Y-27632 in 30% Pluronic gel (Pluronic F-127 Sigma, P2443-1KG) was applied to wounds every day, and then covered the wounds with Telfa sponges (Kendall Health Care, Mansfield, Mass., USA). DMSO was used as a control. All animal studies were reviewed and approved by the International Animal Care and Use Committee of SKKU School of Medicine (SUSM). SUSM is an Association for Assessment and Accreditation of Laboratory Animal Care international accredited facility and abides by the Institute for Laboratory Animal Research guide. Wounds were photographed for 10 days. Immunohistochemistry analyses were performed on 5 µm paraffin embedded sections as described previously (Lin et. al., 2004. Developmental Biology 270, 474-486). Primary antibodies used for immunohistochemistry were mouse anti-α-smooth muscle actin (Sigma, F3777-2ML, 1:500), and mouse anti-PCNA (Santa Cruz Biotechnology, SC-56, 1:500). Secondary antibodies used for immunohistochemistry were EnVision™ Detection System (DAKO, K5007). Masson's trichrome staining was performed according to the manufacturer's instructions (Polysciences Inc., Warrington Pa., USA).

(5.2) Y-27632 Treatment Plays an Important Role in Wound Healing

Figure 23:
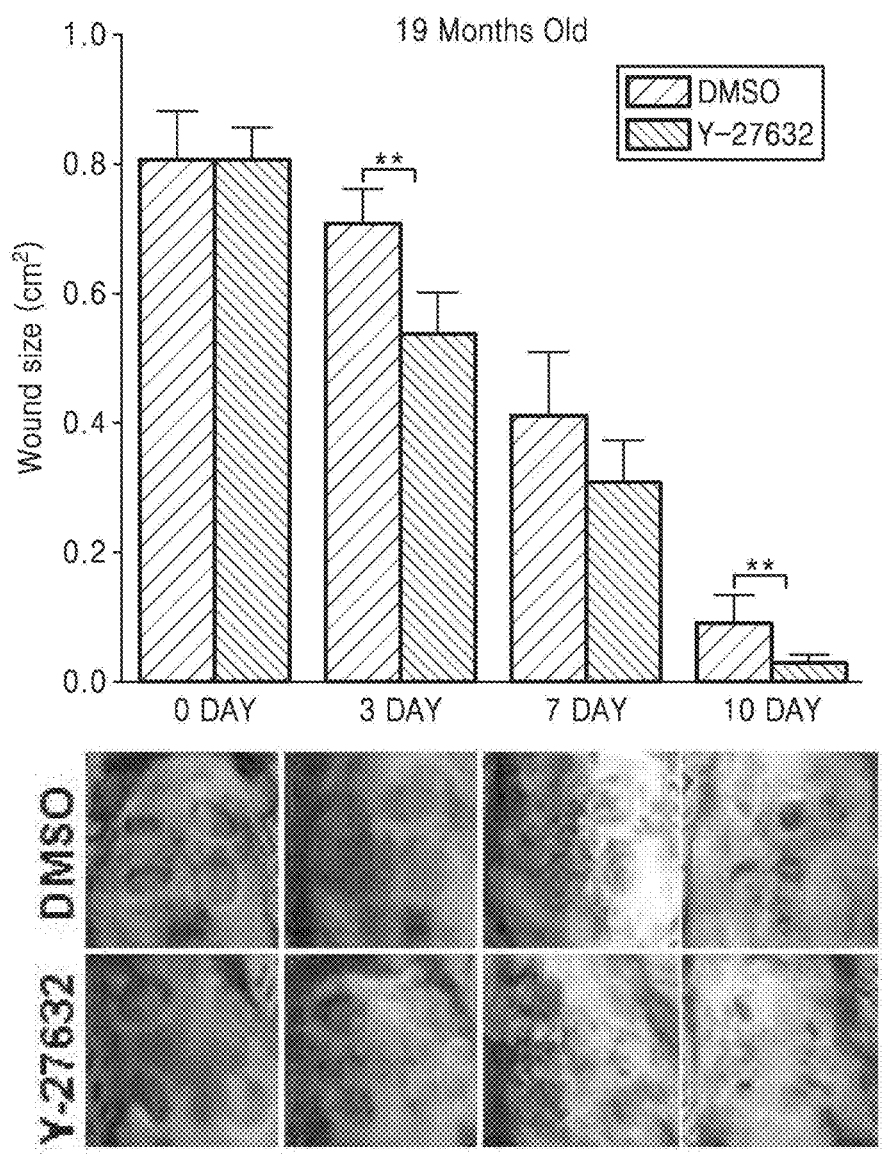
FIG. 23 is a graph and series of images displaying time matched with the wound size and wound appearance of aged mice after applying Y-27632 or DMSO as control.

Aging-dependent impairment of wound healing adversely affects quality of life by decreasing mobility and causing chronic pain. The wound healing effect of Y-27632 in aged mice is known little. The inventors examined the effect of Y-27632 on wound healing in aged mice (19 months old). The macroscopic analysis of time matched DMSO-treated versus Y-27632-treated wounds showed that the wound healing process was markedly accelerated at early points (days 3), compared with controls (FIG. 23: **$P<0.01$). FIG. 23 shows time matched the wound size and wound appearance of aged mice after applying Y-27632 or DMSO as control. According to FIG. 23, on day 10, wound healing was near completion in Y-27632-treated wounds, whereas DMSO-treated wounds still showed remnants of scabs.

An immunohistochemical analysis was carried out to investigate the mechanism underlying the wound-healing process. Sections of the wound area were labeled with an antibody against α-smooth muscle actin (α-SMA), a marker of contractile myofibroblasts expressed during fibrosis. α-SMA immunoreactivity was high in the granulation tissue of control animals, while in the Y-27632-treated group the signal was diffuse in the dermis and was correlated with the appearance of collagen fibers; a strong epidermal signal was correlated with myofibroblast migration into the epidermal region (FIG. 24).

Figure 24:
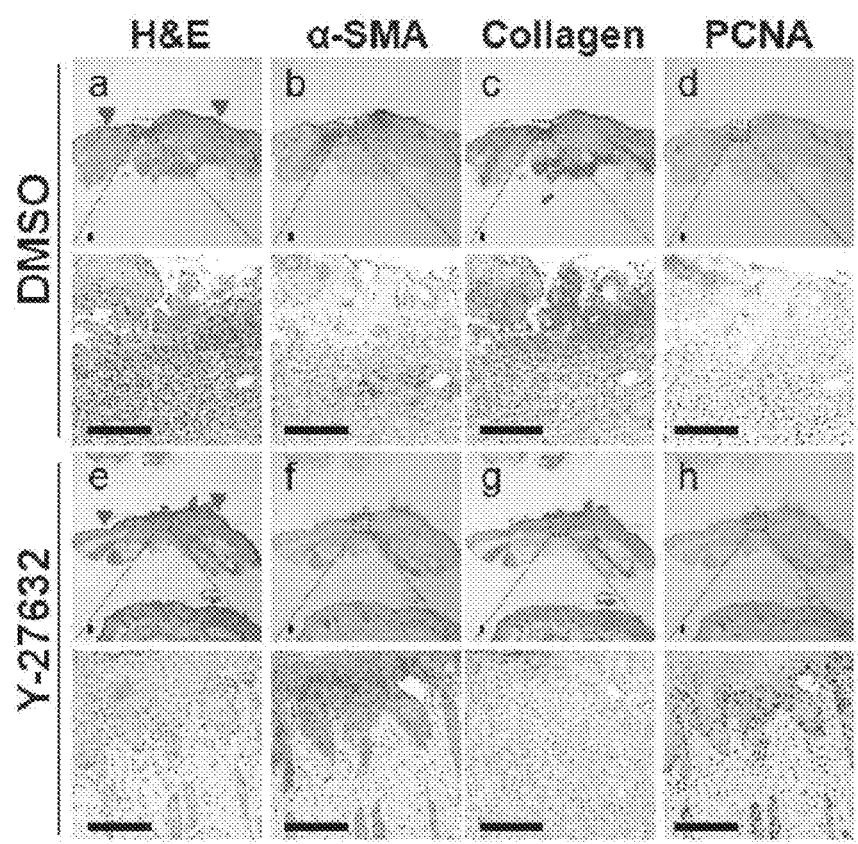
FIG. 24 is an immunohistochemical experimental result showing that Y-27632 treatment plays an important role in wound healing in old mouse (19 months old)

FIG. 24 represents an immunohistochemical experimental result showing that Y-27632 treatment plays an important role in wound healing in old mouse (19 months old). Wound tissue sections were also subjected to Masson's trichrome staining to assess collagen deposition in the cross-sectional area of remodeled tissue. The staining was diffuse in the granulation tissue in the DMSO-treated group; however, in Y-27632-treated mice, the staining was strong in the dermis area and was correlated with the maturation/remodeling phase of wound healing (FIG. 24).

Figure 25:
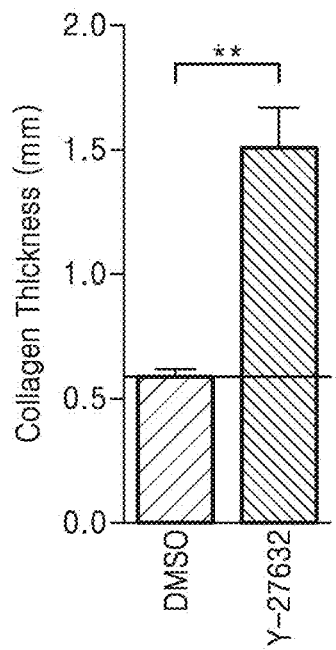
FIG. 25 is a graph displaying experimental results showing that the thickness of collagen deposition in the cross-sectional area of wound remodeling tissue revealed more dense and thicker collagen in the Y-27632 treated wounds compared to DMSO treated wounds in old mice.

Collagen thickness was increased by Y-27632 relative to DMSO treatment (FIG. 25; $P<0.01$). In addition, while DMSO-treated wounds showed selective proliferation in the granulation tissue as determined by proliferating cell nuclear antigen (PCNA) immunolabeling, proliferation was observed in the supra basal area of epidermis of Y-27632-treated wounds (FIG. 24), with a higher number of PCNA-positive cells in the epidermis of the Y-27632-treated than in the control group (FIG. 26; $P<0.01$).

FIG. 25 represents experimental results showing that the thickness of collagen deposition in the cross-sectional area of wound remodeling tissue revealed more dense and thicker collagen in the Y-27632 treated wounds compared to DMSO treated wounds in old mice.

Figure 26:
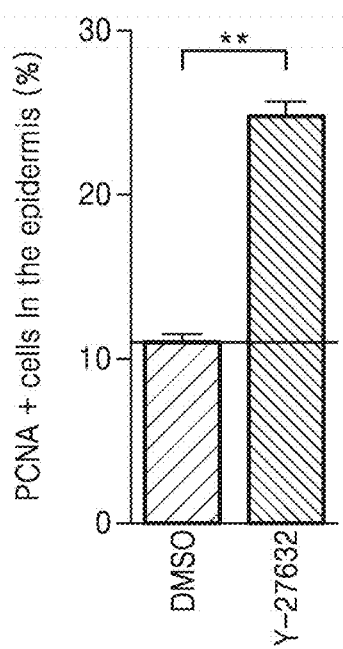
FIG. 26 is a graph displaying experimental results showing the PCNA+ cells in the epidermis in the Y-27632 treated wounds compared to DMSO treated wounds in old mice.

FIG. 26 represents experimental results showing the PCNA+ cells in the epidermis in the Y-27632 treated wounds compared to DMSO treated wounds in old mice.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a symptom associated with a lipofuscin accumulation in a cell in a mammal, the method comprising treating a symptom associated with a lipofuscin accumulation by administering an effective amount of a Rho-kinase inhibitor to the mammal, wherein the symptom associated with lipofuscin accumulation is neuronal ceroid lipofuscinoses (NCL).

2. The method of claim 1, wherein the administering of the Rho-kinase inhibitor is performed by locally administering the Rho-kinase inhibitor to a tissue comprising cells having lipofuscin accumulation.

3. The method of claim 1, wherein the Rho-kinase inhibitor is locally administered to skin tissue, muscle tissue or nerve tissue comprising cells having lipofuscin accumulation.

4. The method of claim 1, wherein the mammal is a human.

5. The method of claim 1, wherein the Rho-kinase inhibitor is (1R,4R)-4-((R)-1-aminoethyl)-N-(pyridin-4-yl)cyclohexanecarboxamide (Y-27632), N-[2-[2-(dimethylamino)ethoxy]-4-(1H-pyrazol-4-yl)phenyl]-2,3-dihydro-1,4-benzodioxin-2-carboxamide] (SR3677), 5-(1,4-diazepane-1-sulfonyl)isoquinoline (Fasudil), a pharmaceutically acceptable salt thereof, a stereoisomer thereof, or combination thereof.

* * * * *